US012582115B2

(12) United States Patent
Bischof et al.

(10) Patent No.: US 12,582,115 B2
(45) Date of Patent: Mar. 24, 2026

(54) CRYOPRESERVATIVE COMPOSITIONS AND METHODS

(71) Applicant: REGENTS OF THE UNIVERSITY OF MINNESOTA, Minneapolis, MN (US)

(72) Inventors: John C. Bischof, St. Paul, MN (US); Michael L. Etheridge, St. Louis Park, MN (US); Jeunghwan Choi, Winterville, NC (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 458 days.

(21) Appl. No.: 17/579,369

(22) Filed: Jan. 19, 2022

(65) Prior Publication Data

US 2022/0132835 A1     May 5, 2022

Related U.S. Application Data

(62) Division of application No. 14/775,998, filed as application No. PCT/US2014/028166 on Mar. 14, 2014.

(Continued)

(51) Int. Cl.
*A01N 1/125* (2025.01)
*A01N 1/142* (2025.01)
(Continued)

(52) U.S. Cl.
CPC ............. *A01N 1/125* (2025.01); *A01N 1/142* (2025.01); *A01N 1/162* (2025.01); *A01N 1/168* (2025.01); *C12N 13/00* (2013.01)

(58) Field of Classification Search
None
See application file for complete search history.

(56) References Cited

U.S. PATENT DOCUMENTS

| | | | |
|---|---|---|---|
| 4,890,457 A | 1/1990 | McNally |
| 5,145,769 A | 9/1992 | McNally |

(Continued)

FOREIGN PATENT DOCUMENTS

| | | |
|---|---|---|
| CN | 101744766 A | 6/2010 |
| CN | 102835389 A | 12/2012 |

(Continued)

OTHER PUBLICATIONS

Sun et al, Review on Microwave-Matter Interaction Fundamentals and Efficient Microwave-Associated Heating Strategies , 2016, Materials, 9(231) 1-24 (Year: 2016).*

(Continued)

*Primary Examiner* — Sharmila G Landau
*Assistant Examiner* — Stephanie A McNeil
(74) *Attorney, Agent, or Firm* — Westman, Champlin & Koehler, P.A.; Amanda M. Prose

(57) ABSTRACT

This disclosure describes compositions and methods related to cryoprotection of biomaterial. Generally, the cryoprotective composition includes a cryoprotective agent and magnetic nanoparticles effective for thawing a cryopreserved specimen comprising biomaterial with minimal biomaterial damage. In some embodiments, the composition is effective for thawing a cryopreserved specimen having a minimum dimension of 0.1 mm. Generally, the method includes obtaining a biomaterial cryopreserved with a cryoprotective composition as summarized above, then subjecting the cryopreserved biomaterial to electromagnetic energy of an intensity sufficient to excite the magnetic nanoparticles and thaw the biomaterial.

22 Claims, 16 Drawing Sheets

Related U.S. Application Data

(60) Provisional application No. 61/790,410, filed on Mar. 15, 2013.

(51) Int. Cl.

| | | |
|---|---|---|
| *A01N 1/162* | (2025.01) | |
| *A01N 1/168* | (2025.01) | |
| *C12N 13/00* | (2006.01) | |

(56) References Cited

U.S. PATENT DOCUMENTS

| | | | |
|---|---|---|---|
| 5,328,821 | A | 7/1994 | Fisher et al. |
| 5,660,076 | A | 8/1997 | Jonkka et al. |
| 5,780,295 | A | 7/1998 | Livesey et al. |
| 6,274,303 | B1 | 8/2001 | Wowk |
| 6,303,388 | B1 | 10/2001 | Fahy |
| 6,381,967 | B1 | 5/2002 | Craig |
| 6,773,877 | B2 | 8/2004 | Fahy |
| 6,951,712 | B2 | 10/2005 | Soane |
| 6,994,954 | B2 | 2/2006 | Taylor |
| 7,112,576 | B1 | 9/2006 | Hubel |
| 7,741,018 | B2 | 6/2010 | Fahy |
| 7,824,848 | B2 | 11/2010 | Owen et al. |
| 7,967,839 | B2 | 6/2011 | Flock |
| 8,037,696 | B2 | 10/2011 | Shaham et al. |
| 8,251,885 | B2 | 8/2012 | Ueda et al. |
| 8,790,923 | B2 | 7/2014 | Ennis et al. |
| 8,802,361 | B2 | 8/2014 | Lee et al. |
| 9,339,027 | B2 | 5/2016 | Benson |
| 2001/0039004 | A1 | 11/2001 | Fahy |
| 2005/0016198 | A1 | 1/2005 | Wowk |
| 2009/0004296 | A1 | 1/2009 | Gabbai |
| 2009/0133410 | A1 | 5/2009 | Thorne et al. |
| 2010/0003197 | A1* | 1/2010 | Bikram ............... A61K 49/186 |
| | | | 977/773 |
| 2010/0212331 | A1 | 8/2010 | Critser |
| 2010/0317108 | A1 | 12/2010 | Stojanov |
| 2011/0207112 | A1 | 8/2011 | Burbank et al. |
| 2012/0087868 | A1* | 4/2012 | Todd .................. A61K 41/0052 |
| | | | 977/773 |
| 2012/0276334 | A1 | 11/2012 | Fedynyshyn et al. |
| 2013/0337034 | A1 | 12/2013 | Kosel et al. |
| 2015/0351381 | A1 | 12/2015 | Vom et al. |
| 2016/0015025 | A1 | 1/2016 | Bischof et al. |
| 2017/0350798 | A1 | 12/2017 | Carragher |
| 2018/0192639 | A1 | 7/2018 | Brockbank et al. |

FOREIGN PATENT DOCUMENTS

| | | |
|---|---|---|
| CN | 104396942 A | 3/2015 |
| CN | 104782616 A | 7/2015 |
| CN | 104012521 B | 8/2015 |
| EP | 2381236 A1 | 10/2011 |
| JP | 2011 231021 A | 11/2011 |
| JP | 5515082 B2 | 6/2014 |
| WO | 98/10231 A1 | 3/1998 |
| WO | 2007/077560 A2 | 7/2007 |
| WO | 2011/047380 A2 | 4/2011 |
| WO | 2011/098367 A3 | 8/2011 |
| WO | 2014/085801 A1 | 6/2014 |
| WO | 2014/143961 A1 | 9/2014 |
| WO | 2017143162 A1 | 8/2017 |
| WO | 20170184721 A1 | 10/2017 |
| WO | 2018/073242 A1 | 4/2018 |

OTHER PUBLICATIONS

Bordelon et al., Magnetic nanoparticle heating efficiency reveals magnetostructural differences when characterized with wide ranging and high amplitude alternating magnetic fields, 2011, Journal of Applied Physics, vol. 109, No. 124904, pp. 1-8 (Year: 2011).*

Alonso, J. et al. "FeCo nanowires with enhanced heating powers and controllable dimensions for magnetic hyperthermia" Journal of Applied Physics 117(17) D113 (2015).

Brockbank, Vitrification of Heart Valve Tissues. Springer: New York, NY; 2015. Cover page, title page, table of contents, and pp. 399-421.

Cardoso, "Cryopreservation of rat hepatocytes with disaccharides for cell therapy." Cryobiology, 2017. 78: p. 15-21.

Darques, "Electrochemical control and selection of the structural and magnetic properties of cobalt nanowires", Applied Physics Letters, 2005, 86.

Darques, "Ferromagnetic nanowire-loaded membranes for microwave electronics" Journal of Magnetism and Magnetic Materials, 2009, 321, 2055-2065.

Das, "Tunable High Aspect Ratio Iron Oxide Nanorods for Enhanced Hyperthermia" Journal of Physical Chemistry C, 2016, 120, 10086-10093.

Davis "Toward development of an implantable tissue engineered liver." Biomaterials, 1996. 17(3): p. 365-72.

De Sousa, G., et al. "A multi-laboratory evaluation of cryopreserved monkey hepatocyte functions for use in pharmaco-toxicology." Chem Biol Interact, 1999. 121(1): p. 77-97.

De Vries, R.J., et al., "Bulk droplet vitrification: an approach to improve large-scale hepatocyte cryopreservation outcome." Langmuir, 2018.

Demetriou, "Early clinical experience with a hybrid bioartificial liver." Scand J Gastroenterol Suppl, 1995. 208: p. 111-7.

Demirci, U. and G. Montesano "Cell encapsulating droplet vitrification." Lab on a Chip, 2007. 7: p. 1428-1433.

Ehrlich, L.E., et al., Thermal Analyses of a Human Kidney and a Rabbit Kidney During Cryopreservation by Vitrification. J Biomech Eng, 2018. 140(1).

Eisenberg, "Stress—Strain Measurements in Vitrified Arteries Permeated With Synthetic Ice Modulators" J Biomech Eng. Aug. 2015.

Eisenberg, "Thermomechanical Stress in Cryopreservation Via Vitrification With Nanoparticle Heating as a Stress-Moderating Effect" J Biomech Eng. Dec. 2015.

Eisenberg, "On the effects of thermal history on the development and relaxation of thermo-mechanical stress in cryopreservation" 2014 Cryogenics (Guildf) 33(4):395-401.

Elliott, "Cryoprotectants: a review of the actions and applications of cryoprotective solutes that modulate cell recovery from ultra-low temperatures" 2017 Cryobiology 76:74-91.

EPA, U.S., Health Advisory for Ethylene Glycol. 1987, Office of Drinking Water Washington, D.C. p. 1-13.

Esmaeily, A. S., et al. "Diameter-modulated ferromagnetic CoFe nanowires" Journal of Applied Physics (2013) 113, 17A327.

Fahy, "Cryopreservation of complex systems: the missing link in the regenerative medicine supply chain" 2006 Rejuvenation Res. 9(2):279-291.

Fahy, G.M., Organ perfusion equipment for the introduction and removal of cryoprotectants. Biomed Instrum Technol, 1994. 28(2): p. 87-100.

Fry, J.R., Bridges, J.W. "The metabolism of 7-ethoxycoumarin in primary maintenance cultures of adult rat hepatocytes." Naunyn Schmiedebergs Arch Pharmacol, 1980. 311(1): p. 85-90.

Geng, "Anisotropic Magnetite Nanorods for Enhanced Magnetic Hyperthermia" Chemistry—An Asian Journal, 2016, 11, 2996-3000.

Ghemes, A. et al. "Controlled Eletrodeposition and Magnet Properties of Co35Fe65 Nanowires with High Saturation Magnetization" Journal of The Electrochemical Society, 164 (2) D13-D22 (2017).

Giwa, "The promise of organ and tissue preservation to transform medicine" 2017 Nat. Biotechnol. 35(6):530-542.

Hahn, Heat Conduction. Wiley: Hoboken, NJ; 2012. Cover page, title page, table of contents.

Hansen "Cytochrome P450 enzyme activity and protein expression in primary porcine enterocyte and hepatocyte cultures." Xenobiotica, 2000. 30(1): p. 27-46.

Hergt, "Magnetic particle hyperthermia—biophysical limitations of a visionary tumour therapy" Journal of Magnetism and Magnetic Materials, 2007, 311, 187-192.

(56) References Cited

OTHER PUBLICATIONS

Hewitt, "Chapter 2: Cryopreservation of Hepatocytes." Methods Mol Biol, 2015. 1250: p. 13-26.

Hurley, "Predictable Heating and Positive MRI Contrast from a Mesoporous Silica-Coated Iron Oxide Nanoparticle" Molecular Pharmaceutics, 2016, 13, 2172-2183.

Iansante, "Human hepatocyte transplantation for liver disease: current status and future perspectives." Pediatric Research, 2017. 83: p. 232.

Ibars, "Hepatocyte transplantation program: Lessons learned and future strategies." World journal of gastroenterology, 2016. 22(2): p. 874-886.

Incropera, Fundamentals of Heat and Mass Transfer. Hoboken: Wiley, 1996. Cover page, title page and table of contents.

Jain et al., "Improved preservation of warm ischemic livers by hypothermic machine perfusion with supplemented University of Wisconsin solution." J Invest Surg, 2008. 21(2): p. 83-91.

Jitraruch "Cryopreservation of Hepatocyte Microbeads for Clinical Transplantation." Cell Transplant, 2017. 26(8): p. 1341-1354.

Kern, "Drug metabolism in hepatocyte sandwich cultures of rats and humans." Biochem Pharmacol, 1997. 54(7): p. 761-72.

Khosla, K. et al. "Gold Nanorod Induced Warming of Embryos from the Cryogenic State Enhances Viability." ACS nano, 2017. 11(8): p. 7869-7878.

Koostra, G., J. Kievit, and A. Nederstigt, Organ donors: heartbeating and non-heartbeating. World J Surg, 2002. 26(2): p. 181-4.

Kuleshova, L.L., et al., Vitrification of encapsulated hepatocytes with reduced cooling and warming rates. Cryo Letters, 2004. 25(4): p. 241-54.

Kumar, B.K., et al., The effects of over expressing aquaporins on the cryopreservation of hepatocytes. Cryobiology, 2015. 71(2): p. 273-8.

Lee, "Extracorporeal liver support devices for listed patients." Liver Transplantation, 2016. 22(6): p. 839-848.

Lewis, "The Grand Challenges of Organ Banking: proceedings from the first global summit on complex tissue cryopreservation" 2016 Cryobiology 72(2):169-182.

Li, A.P., Human hepatocytes: isolation, cryopreservation and applications in drug development. Chem Biol Interact, 2007. 168(1): p. 16-29.

Lin, "Shape effects of iron nanowires on hyperthermia treatment" Journal of Nanomaterials, 2013.

Liu, X. et al. "Dual Suppression Effect of Magnetic Induction Heating and Microencapsulation on Ice Crystallization Enables Low-Cryoprotectant Vitrification of Stem Cell-Alginate hydrogel Constructs" ACS Appl Mater Interfaces. May 16, 2018; 10(19): 16822-16835.

Magalhães, "Vitrification Successfully Preserves Hepatocyte Spheroids." Cell Transplantation, 2008. 17(7): p. 813-828.

Mazur, "Cryopreservation of the germplasm of animals used in biological and medical research: importance, impact, status, and future directions." Biology of reproduction, 2008. 78(1): p. 2-12.

Morales, "Surface and Internal Spin Canting in γ-Fe2O3 Nanoparticles" Chemistry of Materials, 1999, 11, 3058-3064.

Morgan, "Use of trapezoidal waves and complementary static fields incident on magnetic nanoparticles to induce magnetic hyperthermia for therapeutic cancer treatment" Journal of Applied Physics, 2011, 109.

Nemati, "Improving the Heating Efficiency of Iron Oxide nanoparticles by Tuning Their Shape and Size" Journal of Physical Chemistry C, 2018, 122, 2367-2381.

Nicolas, "Concise Review: Liver Regenerative Medicine: From Hepatocyte Transplantation to Bioartificial Livers and Bioengineered Grafts." Stem cells (Dayton, Ohio), 2017. 35(1): p. 42-50.

Jordan, "Increase of the specific absorption rate (SAR) by magnetic fractionation of magnetic fluids" 2003 Journal of Nanoparticle Research, 5(5):597-600.

Jordan, "Inductive heating of ferrimagnetic particles and magnetic fluids: physical evaluation of their potential for hyperthermia" 1993 International Journal of Hyperthermia, 9(1):51-68.

Kalambur, In vitro characterization of movement, heating and visualization of magnetic nanoparticles for biomedical applications. 2005 Nanotechnology 16:1221-33.

Kalambur, "Multifunctional magnetic nanoparticles for biomedical applications" 2007 SPIE; San Jose, CA.

Kalambur, "Cellular level loading and heating of superparamagnetic iron oxide nanoparticles" 2007 Langmuir: the ACS journal of surfaces and colloids 23(24):12329-36.

Kallumadil, "Suitability of commercial colloids for magnetic hyperthermia" 2009 Journal of Magnetism and Magnetic Materials 321(10):1509-13.

Karlsson, "Long-term storage of tissues by cryopreservation: critical issues" 1996 Biomaterials, 17(3):243-56.

Kim, "Nanomedicine" 2010 The New England Journal of Medicine, 363(25):2434-43.

Kline, "Biocompatible high-moment FeCo—Au magnetic nanoparticles for magnetic hyperthermia treatment optimization" 2009 Journal of Magnetism and Magnetic Materials 321(10):1525-8.

Lin, "Critical Considerations in the Biomedical Use of Mesoporous Silica Nanoparticles" 2012 The Journal of Physical Chemistry Letters 3(3):364-74.

Lu "Magnetic nanoparticles: synthesis, protection, functionalization, and application" 2007 Angewandte Chemie International Edition 46(8):1222-44.

Lubner, editor. Measurement of the thermal conductivity of submillimeter biological tissues. ASME IMECE; 2012; Houston: ASME.

Luo, "Development of a single mode electromagnetic resonant cavity for rewarming of cryopreserved biomaterials" 2006 Cryobiology, 53(2):288-93.

Luyet. Chapter III. The vitreous state, vitrification, devitrification and vitromelting. Life and Death and Low Temperatures. Normandy, Missouri: Biodynamica; 1940. p. 221 (Summary).

Manson, "Behavior of Materials Under Conditions of Thermal Stress" 1954 NACA Report 1170:317-350.

Marsland, "Dielectric measurements for the design of an electromagnetic rewarming system" 1987 Cryobiology 24(4):311-23.

Mazur, "Freezing of living cells: mechanisms and implications" 1984 American Journal of Physiology-Cell Physiology, 247(3):C125-C42.

Mehl, "Nucleation and Crystal Growth in a Vitrification Solution Tested for Organ Cryopreservation by Vitrification," 1993 Cryobiology, 30(5):509-18.

Moscoso-Londono, "Structural and magnetic behaviour of ferrogels obtained by freezing thawing of polyvinyl alcohoVpoly(acrylic acid)(PAA)-coated iron oxide nanoparticles" Feb. 2, 2013 European Polymer Journal, 49(2); 279-289.

O'Handley, Modern magnetic materials: principles and applications: Wiley; 2000. 740 p.

Patent Application No. PCT/US2014/028166, filed Mar. 14, 2014; International Preliminary Report on Patentability, issued Sep. 24, 2015; 9 pages.

Patent Application No. PCT/US2014/028166, filed Mar. 14, 2014; International Search Report and Written Opinion, issued Aug. 6, 2014; 14 pages.

Pegg, "Fractures in cryopreserved elastic arteries," 1997 Cryobiology, 34(2):183-92.

Pegg, "Principles of cryopreservation" 2007 Methods Mol Biol., 368:39-57.

Peyridieu, "Critical cooling and warming rates to avoid ice crystallization in small pieces of mammalian organs permeated with cryoprotective agents" 1996 Cryobiology, 33(4):436-46.

Polyak, "High field gradient targeting of magnetic nanoparticle-loaded endothelial cells to the surfaces of steel stents" 2008 PNAS, 105(2), 698-703.

Prow, "Ocular nanoparticle toxicity and transfection of the retina and retinal pigment epithelium" 2008 Nanomedicine: Nanotechnology, Biology And Medicine, 4:340-349.

Qin, "Thermophysical and biological responses of gold nanoparticle laser heating," 2012 Chem Soc Rev 41(3):1191-217.

Qin, "Significantly improved analytical sensitivity of lateral flow immunoassays by using thermal contrast" 2012 Angew Chem Int Ed Engl., 51(18):4358-61.

(56) References Cited

OTHER PUBLICATIONS

Rabin, Ch. 13. Solid Mechanics Aspects of Cryobiology. In: Baust JB, Baust JM, editors. Advances in Biopreservation. Boca Raton: CRC Press / Taylor & Francis; 2007.

Rabin, "Cryomacroscopy of vitrification, Part I: A prototype and experimental observations on the cocktails VS55 and DP6," 2005 Cell Preservation Technology 3(3):169-83.

Rall, "Mouse prepro-epidermal growth factor synthesis by the kidney and other tissues," 1985 Nature, 313(5999):228-31.

Rall, "Ice-free cryopreservation of mouse embryos at −196 degrees C by vitrification," 1985 Nature 313(6003):573-5.

Robinson, "Rapid electromagnetic warming of cells and tissues," 1999 IEEE Transactions on Biomedical Engineering 46(12):1413-25.

Robinson, "Electromagnetic re-warming of cryopreserved tissues: effect of choice of cryoprotectant and sample shape on uniformity of heating," Physics in medicine and biology. 2002;47(13):2311-25.

Roca, "Structural and magnetic properties of uniform magnetite nanoparticles prepared by high temperature decomposition of organic precursors" 2006 Nanotechnolog 17(11):2783-88.

Rondeau, "Slush Baths," 1966 Journal of Chemical & Engineering Data, 11(1):124-.

Rosensweig, "Heating magnetic fluid with alternating magnetic field" 2002 Journal of Magnetism and Magnetic Materials, 252:370-4.

Ruggera, "Rapid and uniform electromagnetic heating of aqueous cryoprotectant solutions from cryogenic temperatures," Cryobiology. 1990;27(5):465-78.

Schmidt, "Acellular vascular tissues: natural biomaterials for tissue repair and tissue engineering" 2000 Biomaterials 21(22):2215-31.

Shah, "Blood-Nanoparticle Interactions and in Vivo Biodistribution: Impact of Surface PEG and Ligand Properties" Aug. 6, 2012 Mol Pharm. 9(8):2146-2155.

Song, "Vitreous preservation of articular cartilage grafts" 2004 Journal of investigative surgery: the official journal of the Academy of Surgical Research, 17(2):65-70.

Song, "Vitreous cryopreservation maintains the function of vascular grafts" 2000 Nature Biotechnology 18(3):296-9.

Stauffer, "Magnetic induction heating of ferromagnetic implants for inducing localized hyperthermia in deep-seated tumors," 1984 Biomedical Engineering, IEEE Transactions on. (2):235-51.

Steif, "Cryomacroscopy of vitrification, Part II: Experimental observations and analysis of fracture formation in vitrified VS55 and DP6" 2005 Cell preservation technology 3(3):184-200.

Steif, "The Effect of Temperature Gradients on Stress Development during Cryopreservation via Vitrification" 2007 Cell Preserv. Technol. 5:104-115.

Taylor "Vitrification in Tissue Preservation: New Developments," Life in the Frozen State: CRC Press; 2004.

Tietze "Visualization of superparamagnetic nanoparticles in vascular tissue using XmuCT and histology" 2011 Histochem Cell Biol 135(2):153-8.

Wang, "Numerical simulation of the effect of superparamagnetic nanoparticles on microwave rewarming of cryopreserved tissues" Feb. 13, 2014 Cryobiology, 68:234-243.

Wowk, "Vitrification enhancement by synthetic ice blocking agents," 2000 Cryobiology, 40(3):228-36.

Atkinson, "Usable frequencies in hyperthermia with thermal seeds" 1984 IEEE Trans on Biomedical Engineering., 31(1):70-5.

Baicu, "Cryopreservation of carotid artery segments via vitrification subject to marginal thermal conditions: correlation of freezing visualization with functional recovery" 2008 Cryobiology., 57(1):1-8.

Baicu, "Vitrification of Carotid Artery Segments: An Integrated Study of Thermophysical Events and Functional Recovery Toward Scale-Up for Clinical Applications" 2006 Cell preservation technology, 4(4):236-44.

Baudot, "Glass-forming tendency in the system water-dimethyl sulfoxide," 2000 Cryobiology, 40(2):151-8.

Belete, "Novel aqueous nano-scaled formulations of oleic acid stabilized hydrophobic superparamagnetic iron oxide nanocrystals" Feb. 2013 Drug Development And Industrial Pharmacy, 39(2):186-196.

Bischof, "Effects of cooling rate and glycerol concentration on the structure of the frozen kidney: assessment by cryo-scanning electron microscopy" 1990 Cryobiology, 27(3):301-10.

Bischof, "Use of X-ray tomography to map crystalline and amorphous phases in frozen biomaterials" 2007 Annals of biomedical engineering, 35(2):292-304.

Bischof, "Quantitative measurement and prediction of biophysical response during freezing in tissues" 2000 Annu Rev Biomed Eng., 2:257-88.

Bordelon De, "Modified solenoid coil that efficiently produces high amplitude AC magnetic fields with enhanced uniformity for biomedical applications" 2012 Magnetics, IEEE Transactions on., 48(1):47-52.

Boutron, "Theoretical prediction of devitrification tendency: determination of critical warming rates without using finite expansions" 1990 Cryobiology, 27(4):359-77.

Boutron, "More accurate determination of the quantity of ice crystallized at low cooling rates in the glycerol and 1,2-propanediol aqueous solutions: comparison with equilibrium" 1984 Cryobiology, 21(2):183-91.

Burdette, "Kidney model for study of electromagnetic thawing" 1978 Cryobiology, 15(2):142-51.

Burdette, "Microwave thawing of frozen kidneys: A theoretically based experimentally-effective design" 1980 Cryobiology, 17(4):393-402.

Choi, "Review of biomaterial thermal property measurements in the cryogenic regime and their use for prediction of equilibrium and non-equilibrium freezing applications in cryobiology" 2010 Cryobiology, 60(1):52-70.

Choi, "A quantitative analysis of the thermal properties of porcine liver with glycerol at subzero and cryogenic temperatures" 2008 Cryobiology, 57(2):79-83.

Choi, "A quantitative analysis on the thermal properties of phosphate buffered saline with glycerol at subzero temperatures" Feb. 29, 2008 Int J of Heat and Mass Transfer, 51(3):640-649.

Claycomb, "HL-1 cells: a cardiac muscle cell line that contracts and retains phenotypic characteristics of the adult cardiomyocyte" 1998 Proc Natl Acad Sci U S A, 95(6):2979-84.

Deng, "Rapid electromagnetic rewarming of cryopreserved tissues using nano-magnetoparticlesfeasibility study" 2008 Proceedings of the 2nd International Conference on Integration and Commmercialization of Micro and Nanosystems, 427-428.

Dennis, "Nearly complete regression of tumors via collective behavior of magnetic nanoparticles in hyperthermia" 2009 Nanotechnology, 20(39).

Dvorak, "Identification and characterization of the blood vessels of solid tumors that are leaky to circulating macromolecules" 1988 The American journal of pathology, 133(1).

Eastman, "Thermal Transport in Nanofluids" 2004 Annu Rev Mater Res., 34:219-46.

Echlin, Low temperature microscopy and analysis. New York, NY: Plenum Press; 1992.

Etheridge, Superparamagnetic Iron Oxide Nanoparticle Heating: A Basic Tutorial. Nanoparticle Heat Transfer and Fluid Flow. New York, NY: CRC Press; 2012. p. 97-121.

Etheridge, "Optimizing Magnetic Nanoparticle Based Thermal Therapies Within the Physical Limits of Heating" 2013 Annals of Biomedical Engineering, 41(1):78-88.

Etheridge, The Big Picture on Nanomedicine: The State of Investigational and Approved Nanomedicine Products: 2013 Nanomedicine: Nanotechnology, Biology and Medicine 9(1):1-14.

Etheridge, "Methods for Characterizing Convective Cryoprobe Heat Transfer in Ultrasound Gel Phantoms" 2013 Journal of Biomechanical Engineering, 135:021001:1-10.

Etheridge, "Radiofrequency heating of magnetic nanoparticle cryoprotectant solutions for improved cryopreservation protocols" 2013 Cryobiology, 67:398-399.

(56)          References Cited

OTHER PUBLICATIONS

Etheridge, "Radiofrequency heating of magnetic nanoparticle cryoprotectant solutions for improved cryopreservation protocols" Presentation slides, Oct. 18, 2012.

Etheridge, "Radiofrequency heating of magnetic nanoparticle cryoprotectant solutions for improved cryopreservation protocols" Jun. 26-29, 2013, ASME Summer Bioengineering Conference, Sunriver OR.

Evans, "Electromagnetic rewarming: the effect of CPA concentration and radio source frequency on uniformity and efficiency of heating" 2000 Cryobiology, 40(2):126-38.

Fahy, "Cryopreservation of the mammalian kidney. II. Demonstration of immediate ex vivo function after introduction and removal of 7.5 M cryoprotectant" 1997 Cryobiology, 35(2):114-31.

Fahy, "Vitrification as an approach to cryopreservation" 1984 Cryobiology, 21(4):407-26.

Fahy, "Physical problems with the vitrification of large biological systems" 1990 Cryobiology, 27(5):492-510.

Fahy, "Physical and biological aspects of renal vitrification" 2009 Organogenesis, 5(3):167-175.

Fahy, Improved vitrification solutions based on the predictability of vitrification solution toxicity. 2004 Cryobiology, 48(1):22-35.

Fahy, "Cryopreservation of organs by vitrification: perspectives and recent advances" 2004 Cryobiology 48(2):157-178.

Fahy, "Vitrification: a new approach to organ cryopreservation" 1986 Progress in Clinical and Biological Research, 224:305-35.

Gerlowski, "Microvascular permeability of normal and neoplastic tissues" 1986 Microvascular Research, 31(3):288-305.

Gneveckow, "Description and characterization of the novel hyperthermia-and thermoablation-system MFH300F for clinical magnetic fluid hyperthermia" 2004 Medical Physics, 31.

Goiti, "Effect of magnetic nanoparticles on the thermal properties of some hydrogels" 2007 Polymer Degradation And Stability, 92:2198-2205.

Han, "Engineering challenges in tissue preservation" 2004 Cell Preservation Technology, 2(2):91-112.

Han, "Numerical simulation of the microwave rewarming process of cryopreserved organs" 2005 Microwave and Optical Technology Letters, 46(3):201-205.

Harvey, Properties of Ice and Supercooled Water. CRC Handbook of Chemistry and Physics 2012-2013. Boca Raton, FL: CRC Press; 2012. p. 6-12.

He, Analysis of thermal stress in cryosurgery of kidneys. 2005 J Biomech Eng. 127(4):656-661.

He, "Investigation of the thermal and tissue injury behaviour in microwave thermal therapy using a porcine kidney model" 2004 International Journal of Hyperthermia, 20(6):567-593.

Hergt, "Physical limits of hyperthermia using magnetite fine particles," 1998 Magn. IEEE Trans. On 34:3745-3754.

Hou, "Magnetic nanohydroxyapatite/PVA composite hydrogels for promoted osteoblast adhesion and prolyferation" Mar. 2013 Colloids And Surfaces B: Biointerfaces, 103(1):318-325.

Jimenez Rios, "Thermal expansion of blood vessels in low cryogenic temperatures, Part I: A new experimental device," 2006 Cryobiology 52(2):269-283.

Jimenez Rios, "Thermal Expansion of blood vessels in low cryogenic temperatures, Part II: Vitrification with VS55, DP6, and 7.05 M DMSO," 2006 Cryobiology 52:284-294.

Johannsen, "Morbidity and quality of life during thermotherapy using magnetic nanoparticles in locally recurrent prostate cancer: Results of a prospective phase I trial" 2007 International Journal of Hyperthermia, 23(3):315-23.

Wusteman, "Vitrification of large tissues with dielectric warming: biological problems and some approaches to their solution," 2004 Cryobiology, 48(2):179-89.

Wusteman, "Vitrification media: toxicity, permeability, and dielectric properties," 2002 Cryobiology, 44(1):24-37.

Wusteman, "Vitrification of rabbit tissues with propylene glycol and trehalose," 2008 Cryobiology, 56(1):62-71.

Zeng, "Fe/Fe oxide nanocomposite particles with large specific absorption rate for hyperthermia" 2007 Applied Physics Letters, 90(23):233112.

Said et al. "Utility of Magnetic Cell Separation as a Molecular Sperm Preparation Technique" Journal of Andrology, vol. 29, No. 2, Mar./Apr. 2008.

Bordelon, D.E. "Magnetic nanoparticle heating efficiency reveals magneto-structural differences when characterized with wide ranging and high amplitude alternating magnetic fields" (2011) J. Appl. Phys. 109, 124904.

Bearer, E. L. et al. "A Simple Method for Quick-Freezing" J Electron Microsc Tech., 1986, 3(2): 233-241.

Fuller, B. J., et al. "Biopreservation of hepatocytes: Current concepts on hypothermic preservation, cryopreservation, and vitrification" (2013) CryoLetters 34(3), 432-452.

Manuchehrabadi, "Ultrarapid Inductive RF Metal Foam Rewarming of Vitrified Biomaterials for Regenerative Medicine" Nov. 2018 Annals of Biomedical Eng., 46(11):1857-1869.

International Search Report and Written Opinion issued for PCT/US2020/013956, dated Jun. 2, 2020.

Etheridge, "RF Heating of Magnetic Nanoparticles Improves the Thawing of Cryopreserved Biomaterials" Technology, vol. 2, No. 3 (Sep. 24, 2014), pp. 229-242, XP055608047, DOI: 10.1142/S2339547814500204.

Manuchehrabadi, "Nanowarming of Tissues", Cryobiology, (Dec. 1, 2016), but presented earlier on Jul. 26, 2016 during meeting CRYO2016), pp. 399-443, XP055386203, DOI: 10.1016/j.cryobiol. 2016.09.091.

Rypka, "A novel simplified ultra-rapid freezing technique for cryopreservation of tissue slices", Cryobiology, vol. 52, No. 2 (Apr. 1, 2006), pp. 193-199, XP024943396, DOI: 10.1016/j.cryobiol. 2005.10.012.

De Graff, "Cryopreservation of rat precision-cut liver and kidney slides by rapid freezing and vitrification", Cryobiology, vol. 54, No. 1, (Feb. 24, 2007), pp. 1-12, XP005907232, DOI: 10.1016/j.cryobiol. 2006.09.002.

Halmagyi, "Cryopreservation of Chrysanthemum morifolium (Dendranthema grandiflora Ramat.) using different approaches", Plant Cell Reports, vol. 22, No. 6, (Jan. 1, 2004), pp. 371-375, XP55737332, DOI: 10.1007/S00299-003-0703-9.

Examination Report issued for related EP patent application serial No. 17753905.3, dated Oct. 12, 2020.

Albert, "The effect of temperature and freeze-thaw processes on gold nanorods" Dec. 2009 Nanotechnology 20(50):505502, 6pgs.

Frazier, "Effects of Heating Temperature and Duration by Gold Nanorod Mediated Plasmonic Photothermal Therapy on Copolymer Accululation in Tumor Tissue" 2015 Mol. Pharmaceut., 12:1605-1614.

Kleinhans, "Physical Parameters, Modeling, and Methodological Details in Using IR Laser Pulses to Warm Frozen or Vitrified Cells Ultra-Rapidly" 2015 Cryobiology, 70(2):195-203.

Manuchehrabadi, N. et al. "Improved Tissue Cryopreservation using Inductive Heating of Magnetic Nanoparticles" Sci Transl Med. Mar. 1, 2017; 9(379) eaah4586.

Yong, et al. "Green, biodegradable, underwater superoleophobic wood sheet for efficient oil/water separation." ACS omega 3.2 (Feb. 1, 2018): 1395-1402.

International Search Report and Written Opinion issued for International Patent Application No. PCT/US17/28351 dated Jul. 7, 2017; 14 pages.

International Preliminary Report on Patentability issued for International Patent Application No. PCT/US17/28351 dated Oct. 23, 2018; 7 pages.

International Search Report and Written Opinion issued for PCT/US2019/041366, dated Nov. 14, 2019.

International Search Report and Written Opinion issued for PCT/US2020/019692, dated May 22, 2020.

Jin, "Survivals of mouse oocytes approach 100% after vitrification in 3-fold diluted media and ultra-rapid warming by an IR laser pulse" 2014 Cryobiology, 68(1):419-430.

Khosla, "Modeling Laser Heating of Zebrafish Embryos Containing Gold Nanoparticles (GNP)" NEMB poster, Apr. 17, 2015. 1 pg.

(56) References Cited

OTHER PUBLICATIONS

Rodriguez-Luccioni, "Enhanced reduction in cell viability by hyperthermia induced by magnetic nanoparticles" International Journal of Nanomedicine (2011) 6, 373-380.

Sanz, "Magnetic hyperthermia enhances cell toxicity with respect to exogenous heating" Biomaterials (2017) 114, 62-70.

Noday, "Viscosity of cryoprotective agents near glass transition: a new device, technique, and data on DMSO, DP6, and VS55" 2009 Cryoletters 49(5):663-672.

Panhwar, "Near-infrared laser mediated modulation of ice crystallization by two-dimensional nanosheets enables high-survival recovery of biological cells from cryogenic temperatures" Nanoscale. Jul. 5, 2018;10(25):11760-11774.

Pearce, "Magnetic Heating of Nanoparticles: The Importance of Particle Clustering to Achieve Therapeutic Temperatures" J Nanotechnol Eng Med. Feb. 2013;4(1):110071-1100714.

Pegg, D.E., Principles of cryopreservation. Methods Mol Biol, 2015. 1257: p. 3-19.

Pless-Petig, G. "Serum-Free Cryopreservation of Primary Rat Hepatocytes in a Modified Cold Storage Solution: Improvement of Cell Attachment and Function." Biopreserv Biobank, 2018. 16(4): p. 285-295.

Plitz "The Effect of Thermal Expansion of Ingredients on the Cocktails VS55 and DP6." Cell Preservation Technology, 2004. 2(3): p. 215-226.

Puschmann, E., et al., Liquidus Tracking: Large scale preservation of encapsulated 3-D cell cultures using a vitrification machine. Cryobiology, 2017. 76: p. 65-73.

Rabin, Y. et al., Thermal expansion measurements of cryoprotective agents. Part II: measurements of DP6 and VS55, and comparison with DMSO. Cryobiology, 2003. 46(3): p. 264-70.

Rabin, Y. et al., Thermal expansion measurements of frozen biological tissues at cryogenic temperatures. J Biomech Eng, 1998. 120(2): p. 259-66.

Rachman, Electromagnetic Warming of Cryopreserved Organs. Thesis. Cambridge: University of Cambridge, 1990.

Reddy "Electrochemical synthesis of magnetostrictive Fe—Ga/Cu multilayered nanowire arrays with tailored magnetic response" Adv. Funct. Mater., 2011, 21, 4677-4683.

Reddy "Magnetization reversal mechanisms in 35-nm diameter Fe1—xGax/Cu multilayered nanowires" Appl. Phys., 2012, 111, 3.

Roochvarg, "7-Ethoxycoumarin metabolism in hepatocytes from pre- and postpubescent male rats." Dev Pharmacol Ther, 1992. 18(1-2): p. 81-8.

Sandby-Møller, "Epidermal thickness at different body sites: relationship to age, gender, pigmentation, blood content, skin type and smoking habits" 2003 Acta Derm. Venereol. 83(6):410-413.

Schepers, "Engineering a perfusable 3D human liver platform from iPS cells." Lab Chip, 2016. 16(14): p. 2644-53.

Sharma, "Inducing cells to disperse nickel nanowires via integrin-mediated responses" Nanotechnology, 2015, 26, 135102.

Sharma, "Magnetic Barcode Nanowires for Osteosarcoma Cell Control, Detection and Separation" IEEE Trans. on Magnetics, 2013, 49, 453-456.

Shepherd, "Thickness of human articular cartilage in joints of the lower limb" 1999 Ann. Rheum. Dis. 58(1):27-34.

Shore "Nanowarming Using Au-Tipped Co35Fe65 Ferromagnetic Nanowires" Nanoscale, 2019, 11, 14607-14615.

Shore "Electrodeposited Fe and Fe—Au nanowires as MRI contrast agents" Chemical Communications, 2016, 52, 12634-12637.

Smith, "A comprehensive evaluation of metabolic activity and intrinsic clearance in suspensions and monolayer cultures of cryopreserved primary human hepatocytes." J Pharm Sci, 2012. 101(10): p. 3989-4002.

Sohn, "Optimization of magnetic anisotropy and applied fields for hyperthermia applications." Journal of Applied Physics, 2010, 107.

Solanki, "Thermo-mechanical stress analysis of cryopreservation in cryobags and the potential benefit of nanowarming" 2017 Cryobiology 76:129-139.

Stauffer, "Observations on the use of ferromagnetic implants for inducing hyperthermia" 1984 IEEE Trans. Biomed. Eng. 31(1):76-90.

Steif, "Can thermal expansion differences between cryopreserved tissue and cryoprotective agents alone cause cracking?" 2009 Cryo Letters 30(6):414-421.

Steif, "Continuum mechanics analysis of fracture progression in the vitrified cryoprotective agent DP6" 2008 J. Biomech. Eng. 130(2):21006.

Tong, S. et al. "Size-Dependent Heating of Magnetic Iron Oxide Nanoparticles" ACS Nano. Jul. 25, 2017;11(7):6808-6816.

Vodkin, I. et al. "Extended Criteria Donors in Liver Transplantation." Clin Liver Dis, 2017. 21(2): p. 289-301.

Wang, X., et al., Development of a modified vitrification strategy suitable for subsequent scale-up for hepatocyte preservation. Cryobiology, 2012. 65(3): p. 289-300.

Wildeboer, "On the reliable measurement of specific absorption rates and intrinsic loss parameters in magnetic hyperthermia materials" Journal of Physics D: Applied Physics, 2014, 47, 14.

Wu, Y., et al., Vitreous cryopreservation of cell-biomaterial constructs involving encapsulated hepatocytes. Tissue Eng, 2007. 13(3): p. 649-58.

Xu, H., et al., Inhibition of TXA synthesis with OKY-046 improves liver preservation by prolonged hypothermic machine perfusion in rats. J Gastroenterol Hepatol, 2008. 23(7 Pt 2): p. e212-20.

Zhang, X. et al. "Magnetothermal heating facilitates the cryogenic recovery of stem cell-laden alginate-Fe3O4 nanocomposite hydrogels" Biomater. Sci. Nov. 20, 2018;6(12):3139-3151.

International Patent Application No. PCT/US17/17331, filed Feb. 17, 2017; International Search Report / Written Opinion issued May 8, 2017; 9 pages.

International Patent Application No. PCT/US17/17331, filed Feb. 17, 2017; International Preliminary Report on Patentability issued Aug. 30, 2018; 7 pages.

Etheridge, "Accounting for biological aggregation in heating and imaging of magnetic nanoparticles" Technology, vol. 2, No. 3, Sep. 2014.

Heider, "Magnetic Properties of Hydrothermally Recrystallized Magnetite Crystals" (1987) Science, Reports, 236(4806), pp. 1287-1290.

Larson, "The Structure and Rheology of Complex Fluids", Oxford University Press 1999.

Carrey, "Simple models for dynamic hysteresis loop calculations of magnetic single-domain nanoparticles: Application to magnetic hyperthermia optimization" Journal of Applied Physics 109, 083921 (2011); doi: 10.1063/1.3551582.

* cited by examiner

CRYOPRESERVATIVE COMPOSITIONS AND METHODS

CROSS-REFERENCE TO RELATED APPLICATION

This application is a divisional of and claims priority to U.S. patent application Ser. No. 14/775,998, filed Sep. 14, 2015, which is a § 371 U.S. National Stage of International Application No. PCT/US2014/028166, filed 14 Mar. 2014, which claims priority to U.S. Provisional Patent Application Ser. No. 61/790,410, filed Mar. 15, 2013, each of which is incorporated herein by reference.

GOVERNMENT FUNDING

This invention was made with government support under CBET-1066343 awarded by the National Science Foundation. The government has certain rights in the invention.

SUMMARY

This disclosure describes, in one aspect, a cryoprotective composition. Generally, the cryoprotective composition includes a cryoprotective agent and magnetic nanoparticles effective for thawing a cryopreserved specimen comprising biomaterial with minimal biomaterial damage.

In some embodiments, the composition is effective for thawing a cryopreserved specimen having a minimum dimension of 0.1 mm.

In some embodiments, the magnetic nanoparticles can include superparamagnetic nanoparticles and/or ferromagnetic nanoparticles. In some embodiments, the nanoparticles may be RF-susceptible nanoparticles. In some embodiments, the total concentration of magnetic nanoparticles can be 0.01 mg Fe/mL to 100 mg Fe/mL.

In some embodiments, the composition is effective for thawing a cryopreserved specimen with minimal cracking and/or minimal devitrification.

In some embodiments, the composition is effective for thawing a biomaterial that is suitable for transplantation.

In another aspect, this disclosure describes a composition that includes a biomaterial perfused with and/or suspended in the cryoprotective composition summarized above.

In another aspect, this disclosure describes a method of thawing a cryopreserved biomaterial. Generally, the method includes obtaining a biomaterial cryopreserved with a cryoprotective composition as summarized above, then subjecting the cryopreserved biomaterial to electromagnetic energy of an intensity sufficient to excite the magnetic nanoparticles and thaw the biomaterial.

In some embodiments, the electromagnetic energy can include a radio frequency field, an alternating magnetic field, or a rotating magnetic field.

In some embodiments, the biomaterial is perfused with and/or suspended in the cryoprotective composition.

In some embodiments, the cryoprotective composition has a volume with a minimum dimension of at least 1 mm.

In some embodiments, the biomaterial is thawed with minimal devitrification and/or cracking.

In some embodiments, the biomaterial is warmed at a rate of at least 10° C./minute throughout.

In some embodiments, subjecting the cryopreserved biomaterial to electromagnetic energy generates a thermal gradient of no more than 1° C./mm during within the biomaterial.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. (Left) Methods exist to successfully vitrify bulk systems (organs and thin tissues). However, issues related to devitrification and cracking during thawing of bulk-vitrified samples (Middle) are rate limiting to the technology. (Right) Here we present a new approach to thawing using radiofrequency heating of magnetic nanoparticles (mNPs).

FIG. 14. Modeling the effects of non-uniform mNP distribution. A one-dimensional model (a) demonstrates the effects of non-uniform heat generation within the biomaterial on limiting the minimum heating rate (b) and imposing thermal stresses (c). Included in the plots are the critical warming rate ($v_{crit}$) and critical tensile stress ($\sigma_{tens,crit}$) for VS55. However, the stresses imposed during heating (expansion) will be compressive, so the critical stress is expected to be much higher in compression.

DETAILED DESCRIPTION OF ILLUSTRATIVE EMBODIMENTS

Figure 2:
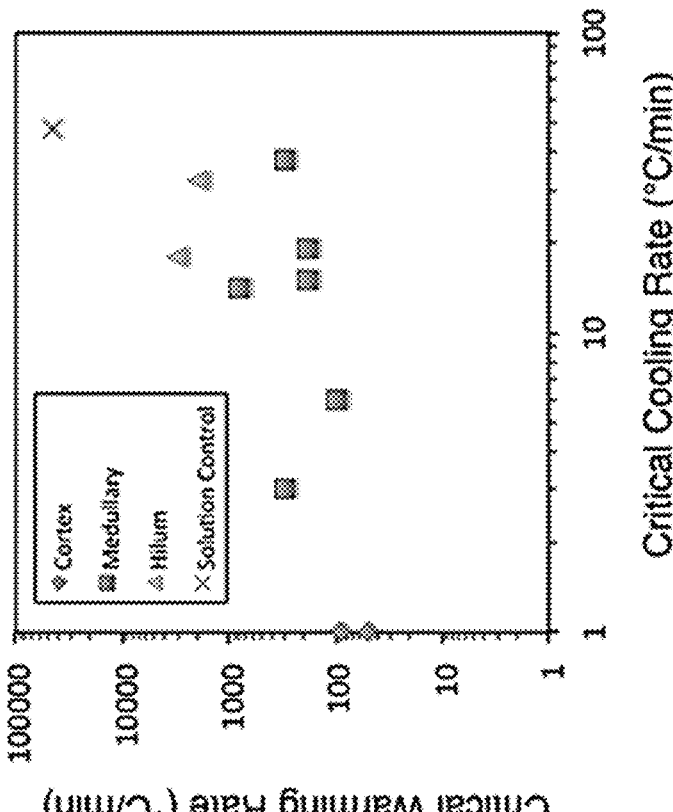
FIG. 2. (Left) Extended phase diagram modified from Fahy et al. *Cryobiology* 21(4):407-426, 1984. (Right). Critical warming versus cooling rates from 10 rabbit kidney samples permeated with 30% 2,3 butanediol (w/w) as described in Peyridieu et al., *Cryobiology* 33(4):436-446, 1996. The reference solution is also given and shown to require a much higher cooling and warming rate than in the tissue. Notice also that various parts of the kidney have equilibrated differently to the same cryoprotective agent yielding different critical rates.
Figure 2:
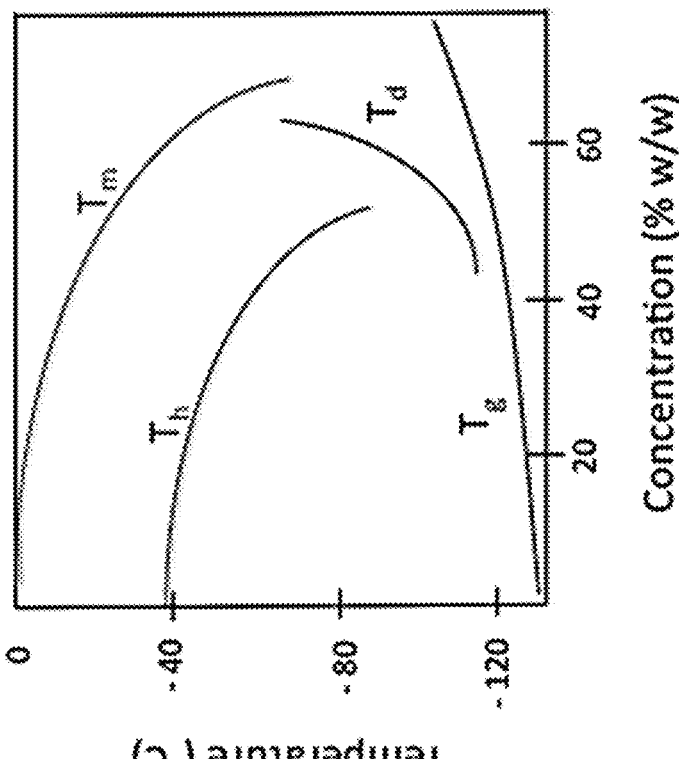

Cryopreservation is commonly used to protect biomaterials such as, for example, a tissue, an organ (e.g., for transplantation), a cell monolayer, or a cell suspension, but may be constrained by the toxicity of cryoprotectant chemicals and/or difficulty in uniformly and rapidly heating and cooling the biomaterial. Adding magnetic nanoparticles to cryoprotectant solutions can allow rapid heating using external radio frequency fields. Since the resulting thawing is rapid and uniform, lower concentrations of cryoprotectants are required and cracking due to thermal stress can be reduced. This can result in lower toxicity and improved viability of cryopreserved biomaterial.

Traditional cryopreservation is limited because of constraints on freezing and thawing biomaterials. Many current techniques allow for sufficiently rapid cooling (sometimes with the addition of high pressure for bulk systems), but they do not allow sufficiently rapid thawing after cryopreservation. The use of cryoprotectant chemicals can decrease the negative effects of, for example, ice crystals forming in the biomaterial during cooling and/or non-uniform and slow thawing. However, cryoprotectants at high concentrations can be toxic to biomaterials.

This disclosure describes methods and compositions involving rapid and uniform heating of cryopreserved biomaterials. This results in lower thermal stresses (e.g., avoiding cracks) and little or no devitrification (e.g., avoiding crystals) on the cryopreserved biomaterial, which can translate to improved survival. Thus, the process may allow a significant reduction in the concentration of cryoprotectants that are required in the cryopreservation process. A reduced concentration of cryoprotectants can extend the application of cryopreservation to larger biomaterials such as, for example, tissue slices, heart valves, and kidneys. The technology also can be used, for example, to preserve blood samples, stem cells, and reproductive biomaterials.

The cryopreservation method described herein uses a cryoprotectant solution that includes magnetic nanoparticles to preserve biomaterials. A biomaterial may be submerged in or perfused with a cryoprotectant solution prior to rapid cooling to a vitreous (a non-crystalline or amorphous) state. External radio frequency fields can be applied for controlled interaction with the magnetic nanoparticles, leading to the rapid generation of heat at nanoparticle sites dispersed throughout the biomaterial. This rapid generation of heat at dispersed sites results in quick and uniform thawing of cryopreserved biomaterial.

Traditional thawing processes allow heating rates of only 1° C.-10° C./min for sample sizes larger than 1 cm in characteristic size. In contrast, the use of radio frequency fields in conjunction with magnetic nanoparticles allows heating rates as high as 100° C.-10,000° C./min (a hundred-to-thousand-fold increase in the heating rate). This rapid thawing allows for the use of lower concentration of cryo-protectant chemicals—e.g., 4 M or lower, compared to current standard cryoprotectant concentrations of 8 M needed for vitrification. Since only certain biomaterials can resist toxic effects that can be caused by the higher 8M concentration of cryoprotectants, the lower concentration of cryoprotectant chemicals needed to protect biomaterials in the methods described herein makes cryopreservation a viable option for a broader scope of biomaterials than is currently possible with vitrification approaches.

Although alternatives to slow boundary convection-based heating (e.g., rapid microwave heating) exist, they have limitations in the uniformity of heating. Spatial differences in the thawing rate through the biomaterial can lead to thermal stresses that can physically damage the biomaterial (e.g., cracking). Such damage may be unacceptable for biomaterials intended for transplantation. The present pro-tocol effectively enhances the heat generation within the cryopreserved system, which significantly improves the rapidity and uniformity of heating, and therefore reduces the amount of cryoprotectant chemical necessary to preserve the biomaterial and/or reduces damage and stress experienced by the biomaterial during the thawing process. The more rapid and more uniform heating and/or reducing the amount of cryoprotectants necessary to preserve biomaterial can reduce the likelihood and/or extent of damage to cryopre-served biomaterials that currently constrain more wide-spread use of cryopreservation.

Vitrification, the freezing to a "glassy" rather than crys-talline phase, is a form of cryopreservation and an important enabling approach for cellular and regenerative medicine. Vitrification offers the ability to store and transport cells, tissues, and/or organs for a great variety of biomedical uses. Our protocol is based on uniform heat generation within the biomaterial and is therefore not dependent on size or con-vective boundary condition and, therefore, overcomes fun-damental limitations experienced with protocols that involve boundary convection or microwave heating. Thus, our pro-tocol can allow one to use cryopreservation for larger volumes of samples that include biomaterials, where devit-rification and/or cracking routinely result in preservation failures using conventional cryopreservation methods. Moreover, faster thaw rates may allow one to reduce the amount of potentially toxic cryoprotective agents needed to avoid devitrification.

Figure 1:
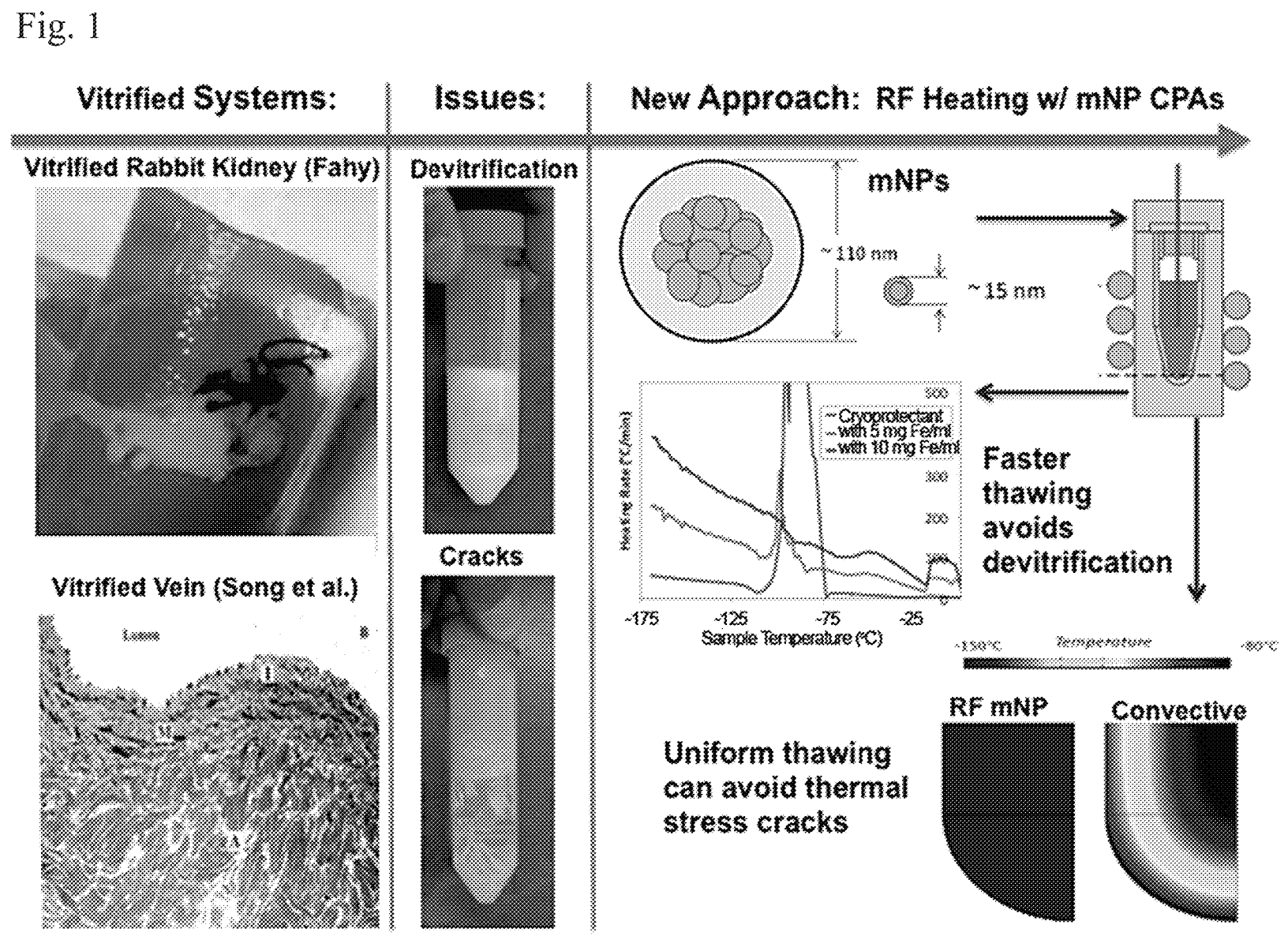
Figure 7:
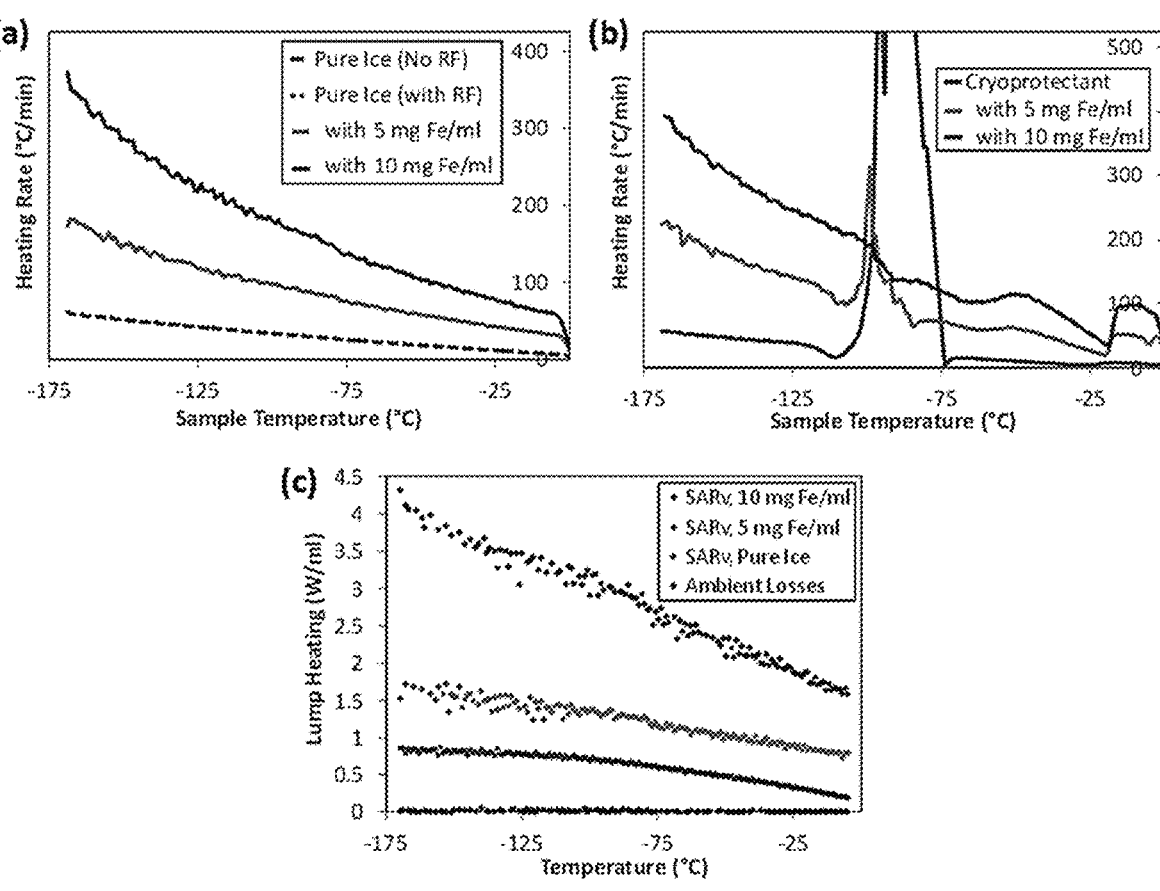
FIG. 7. Observed heating rates in flash frozen, aqueous (a) and [6M glycerol in 1×PBS] (b) mNP solutions subjected to a 20 kA/m and 370 kHz radio frequency field. The ambient losses and volumetric radio frequency heating ($SAR_V$) were also calculated from the aqueous samples based on a lumped approximation (c).
Figure 8:
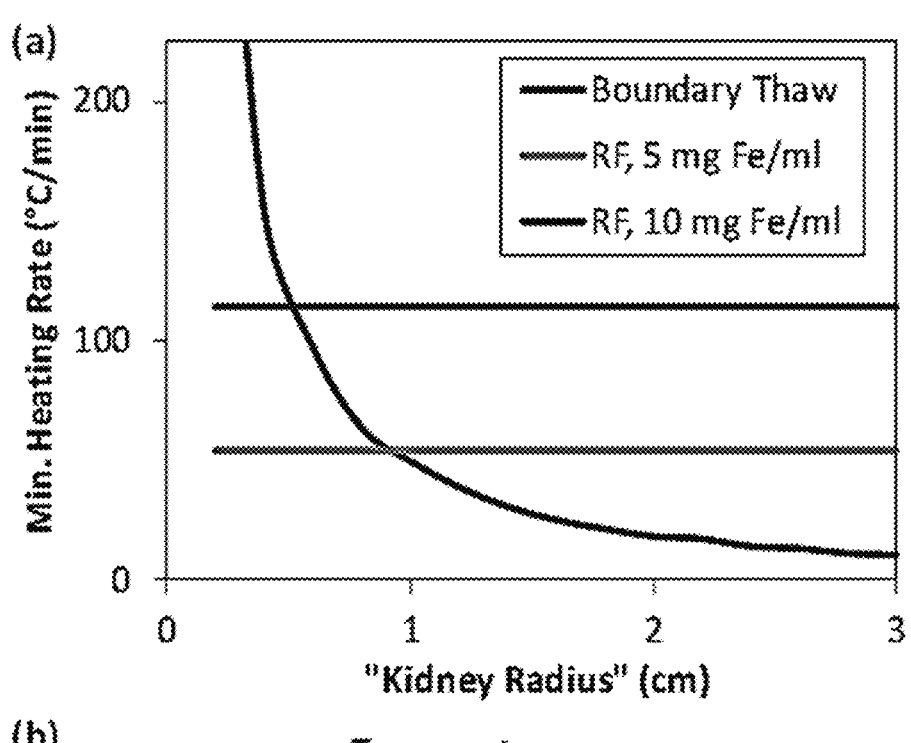
FIG. 8. Simple "kidney" model results, where volumetric radio frequency heating was calculated based on the experimentally measured data (See FIG. 7(c)) and vitrified tissue thermal properties estimated from cryoprotective agent loaded liver properties as described in Choi, J., and J. C. Bischof. *Cryobiology* 57(2):79-83, 2008. The minimum heating rate at the glass transition temperature does not vary with the size of the kidney for the insulated radio frequency heated case (a) and the temperature fields remain uniform (b, right) after 1 minute of heating (r=2 cm) versus a convective boundary warming case (b, left) with h=50 W/m²-K and $T_{env}$=37° C.
Figure 8:
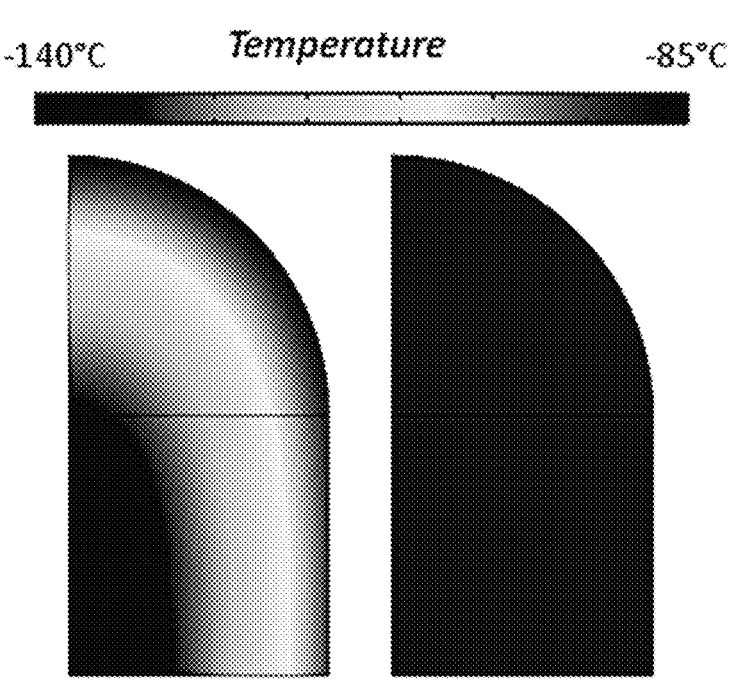
Figure 9:
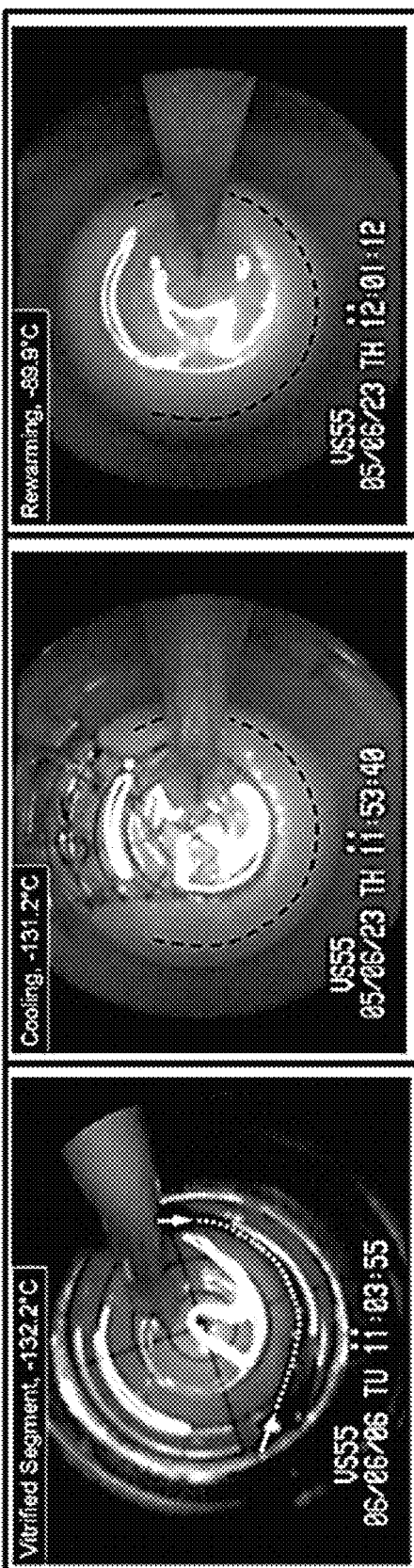
FIG. 9. Cryomacroscopy. (Left) shows a successfully vitrified sample: note grid visibility below sample. Failed samples include: (Middle) with cracking in top of image; and (Right) devitrification as noted by loss of transparency (i.e., grid is no longer visible).

In one aspect, this disclosure describes a new approach for rapidly and uniformly heating vitrified biospecimens through the use of radio frequency (<1 MHz) excited magnetic nanoparticles (mNPs). This technique can increase heating rates by two-to-three orders of magnitude or more over conventional boundary heating and does not depend on the size of the sample. Radio frequency thawing of bioma-terials perfused with or incubated in cryoprotective agents that include magnetic nanoparticles decreases devitrification in cryoprotective agents (6 M glycerol in 1×PBS) magnetic nanoparticle solutions (FIG. 1 and FIG. 7). While existing methods include the use of magnetic nanoparticles in cryo-protective solutions in small dimensions, the challenges described above with respect to uniformity of heating throughout a sample or specimen of larger dimension (e.g., minimum dimension of at least 1 mm (e.g., at least 1-10 mm)) have limited the application of the existing methods.

In some embodiments, the mNP can include a combina-tion of nanoparticles (e.g., a superparamagnetic nanoparticle and a ferromagnetic nanoparticle) to heat in two different cryoprotective agent solutions (glycerol and VS55 (Fahy et al. *Cryobiology* 21(4):407-426, 1984)) under a range of applied fields which can scale to larger systems. Glycerol alone is considered a suboptimal cryoprotective agent because it requires one of the highest critical warming rates to avoid devitrification in 50% w/w cryoprotective agent on thaw (Boutron P. *Cryobiology* 21(2):183-191, 1984). VS 55 can require slower warming and has offered successful vitrification for a number of tissue systems (Table 1).

TABLE 1

Examples of successfully vitrified biomaterials.

| System | Cryoprotective Agent | Cool/Thaw Rate (° C./min) | Method Note | Cite |
|---|---|---|---|---|
| Embryo | VS1 | >20/>300 | >rates best | (a) |
| Vein | VS55 | 43/225 | Annealing < Tg | (b) |
| Artery | VS55 | >70/175 | Annealing < Tg | (c) |
| Kidney | VS55 | 10/300^ | 1000 atm used | (d, e) |

VS1 is very similar to VS55 developed by Fahy (*Cryobiology* 21(4): 407-426, 1984) and studied by DSC by Mehl (*Cryobiology* 30(5): 509-518, 1993).
(^) 300° C./min suggested for EM warming (Ruggera et al. *Cryobiology* 27(5): 465-478, 1990). Importantly, the kidney can be vitrified, but cannot be thawed successfully at present because 300° C./min cannot be achieved in a large mammalian kidney using boundary thawing.
(a) Rall WF, Fahy GM. *Nature.* 1985; 313(6003): 573-575;
(b) Song YC, Khirabadi BS, Lightfoot F, Brockbank KG, Taylor MJ. *Nature biotechnol-ogy.* 2000; 18(3): 296-299;
(c) Baicu S, Taylor MJ, Chen Z, Rabin Y. *Cell preservation technology.* 2006; 4(4): 236-244;
(d) Fahy GM, MacFarlane DR, Angell CA, Meryman HT. *Cryobiology.* 1984; 21(4): 407-426;
(e) Fahy GM, Wowk B, Wu J, Phan J, Rasch C, Chang A, et al. *Cryobiology.* 2004; 48(2): 157-178.

Thus, the use of mNP can extend the abilities of almost any cryopreservation solution currently in use. Cryopreser-vation requires that the biomaterial undergo controlled rate freezing procedures that can damage and potentially destroy cells in suspension, monolayers, or within a tissue or organ. At the cellular level, this injury can involve dehydration and/or intracellular ice formation. These factors are oppo-sitely dependent on the cooling rate: slow cooling can lead to dehydration, fast cooling can produce intracellular ice formation. When taken to extremes, both of these factors are known to reduce cell viability in suspension, but by adding a sufficient molarity of cryoprotective agent, these biophysi-cal processes can be reduced, and in some cases eliminated, through vitrification.

In simple terms vitrification relies on loading a high enough concentration of cryoprotective agent (often 50% or more w/w) and cooling rapidly enough to reach below the glass transition temperature ($T_g$) while minimizing or avoid-ing nucleation of ice ($T_h$) (FIG. 2a). Once below the glass transition temperature, the biomaterial is stable and can be stored. To thaw, one faces a similar challenge in reverse, which is to pass through the devitrification temperature ($T_d$) without allowing crystals to grow. Avoiding ice growth as one moves through the devitrification and liquidus tempera-tures ($T_d$ and $T_m$) can be achieved by increasing both cryoprotective agent concentration and/or thawing rates. Our efforts address the successful thaw from the vitrified state.

The cooling and thawing rates necessary to achieve vitrification and avoid devitrification of small tissue samples have been studied previously. (e.g., Peyridieu et al. *Cryo-biology* 33(4):436-46, 1996). Cooling rates to achieve vit-rification during freezing are typically one to two orders of magnitude less than the thawing rates needed to avoid devitrification upon subsequent thawing (See FIG. 2b). For instance, cryoprotective agent (30% butanediol w/w) can be added to kidney tissue and cooled at 10° C./min to 100° C./min to achieve vitrification followed by thawing at rates 10-fold faster to avoid devitrification (100° C./min to 1000°

C./min) (FIG. 2*b*). As one typically forms some small nuclei upon cooling, one typically thaws the biomaterial more rapidly than the typical cool rate in order to "rescue" the sample from the cooling-initiated nuclei. These warming rates and cooling rates can be studied, for example, in small pieces of kidney since the necessary warming and cooling rates are unachievable in bulk systems using conventional methods.

Figure 3:
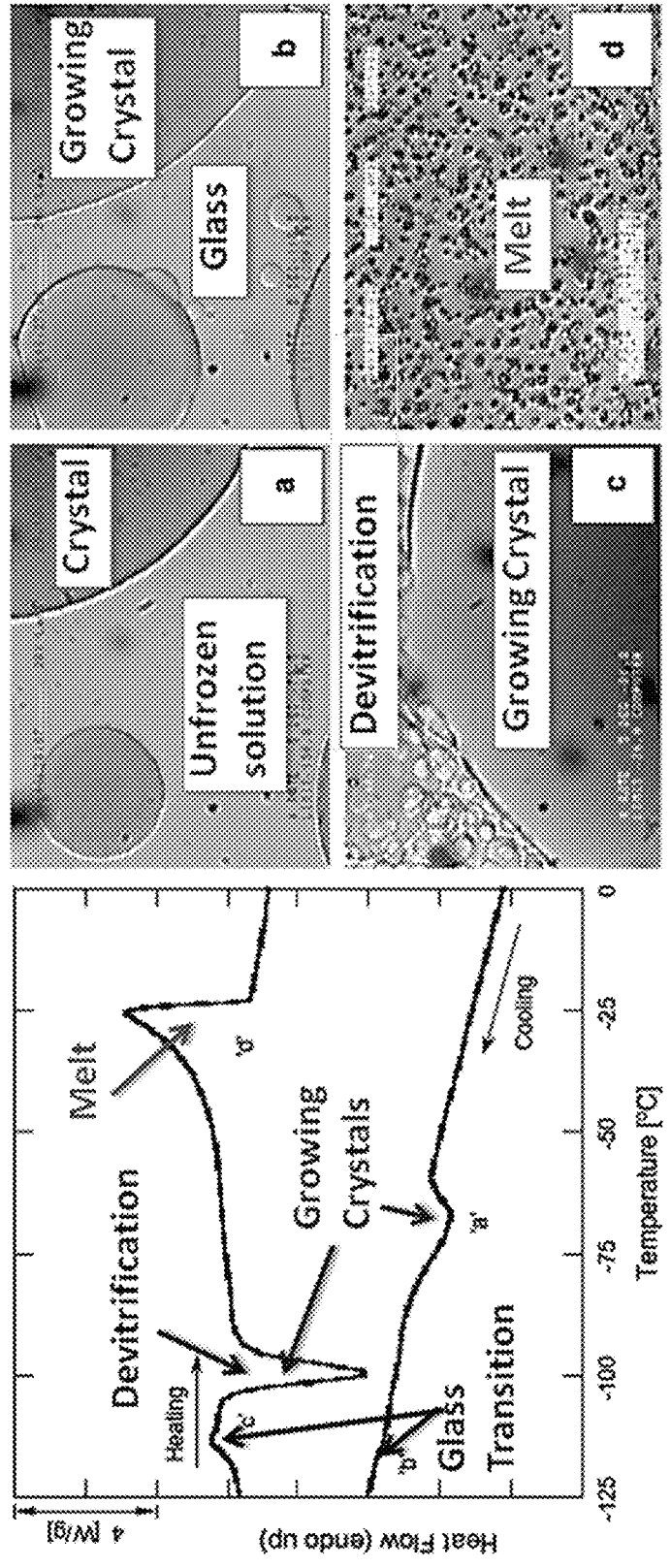
FIG. 3. Enthaplic and cryomicroscopic events during freezing and thawing of 6 M glycerol in 1×PBS without pre-nucleation, as described in Choi, J., and J. C. Bischof. *Int J of Heat and Mass Transfer* 51:640-649, 2007.

Differential Scanning calorimetry (DSC) may be used to quantify the relative amounts of crystallization versus vitrification and the critical cooling rates, and the critical thawing rates in representative smaller volumes of tissues and solution. FIG. 3 shows DSC heat release signatures due to crystallization, vitrification, devitrification (i.e., crystallization upon thaw), and melting in glycerol. Controlled cooling and thawing rates that are accessible by the machine are typically less than 320° C./min and the sample size is usually ≤10 mg in order to avoid thermal lag and allow proper calibration (Choi, J., and J. C. Bischof. *Int J of Heat and Mass Transfer* 51:640-649, 2007; Choi, J., and J. C. Bischof. *Cryobiology* 57(2):79-83, 2008). Thus, the DSC sample pan is typically small and the sample is typically completely contained within a volatile sample pan—i.e., the lid is crimped shut such that no sample loss is possible due to evaporation or volatilization of the sample. As shown in FIG. 3, one can measure crystallization, vitrification ($T_g$), devitrification ($T_d$) and melting ($T_m$).

Figure 4:
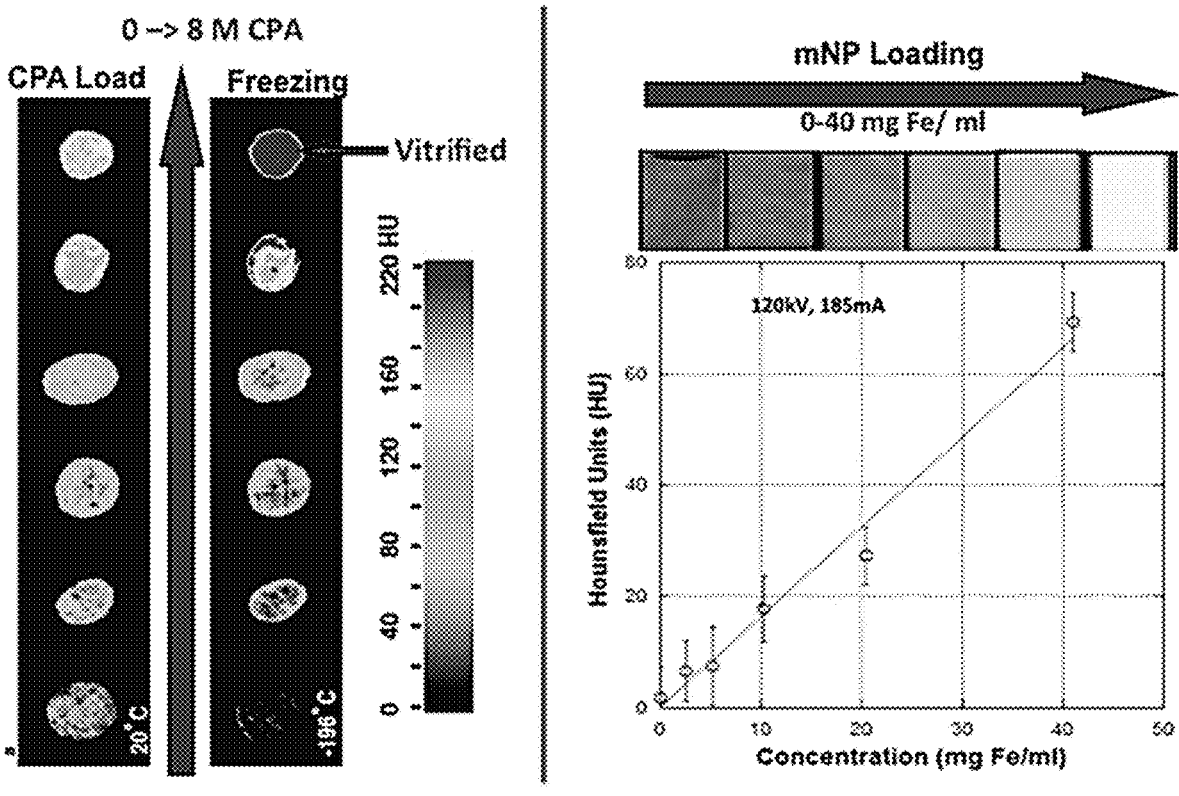
FIG. 4. Computed tomography (CT) of cryoprotective agent loading, freezing (including both crystallization and vitrification) and mNP loading of solutions, as described in Bischof et al. *Ann Biomed Eng* 35(2):292-304, 2007.

Imaging and microscopy methods also can be used to generate complementary information to DSC such as, for example, cryomicroscopy (FIG. 3), freeze-substitution (FIG. 1), and computed tomography (FIG. 4). In the case of cryomicroscopy, one can observe the crystalline versus amorphous material directly and compare the results to DSC. In the case of freeze-substitution, one can directly substitute for the ice using an organic solvent in the cryogenic regime. Finally, one can calibrate the Hounsfield Unit to the crystalline (or amorphous) phase within frozen biomaterials. There can be a roughly 50 HU change between cryoprotective agent loaded and frozen vs. loaded and vitrified material (i.e. the HU change indicates whether the bulk material is vitrified or crystallized).

As both cooling and heating depend at least in part on thermal properties of the materials, one can measure the temperature-dependent thermal properties of the system. Specifically, thermal conductivity can be measured by, for example, pulse decay (Choi, J., and J. C. Bischof. *Int J of Heat and Mass Transfer* 51:640-649, 2007; Choi, J., and J. C. Bischof. *Cryobiology* 57(2):79-83, 2008) or "3 omega" technique (Lubner S D, Choi J W, Hasegawa Y, Fong A, Bischof J C, Dames C, editors. Measurement of the thermal conductivity of sub-millimeter biological tissues. ASME IMECE; 2012; Houston: ASME). Using VS55 as a cryoprotective agent may alter the thermal properties somewhat compared to, for example, glycerol. Because magnetic nanoparticles can be a very small percentage of the sample (<1% by volume), they are unlikely to dramatically alter thermal properties of the cryoprotective agent.

Heating Approaches

Rapid thawing of cellular systems can often be realized by reducing the size of the sample, increasing the conductivity of the sample holder, and/or creating a highly convective environment (e.g., a heated water bath). This has been achieved for sperm, ova, embryos, drosophila embryos, and many smaller systems that can be placed in small containers that are amenable to boundary cooling and thawing (See Table 1 for exemplary sample systems). However, uniform and fast cooling or thawing from the boundary for larger samples (beyond several mm in characteristic dimension) is not possible due to heat transport limitations using conventional techniques (Karlsson J O, Toner M. *Biomaterials* 17(3):243-256, 1996).

One alternative to boundary cooling and thawing involves volumetric heating, in which the rates of thawing are related directly to the applied heat generation (u′′′ or specific absorption rate (SAR), W/m³):

$$\frac{dT}{dt} = \frac{u'''}{\rho c_p} \text{ and } u''' = SAR_v \sim \left[\frac{W}{m^2}\right] \qquad (1)$$

where T is temperature, t is time, $\rho$ is density and $c_p$ is specific heat. Heating rate (dT/dt) can be constant through the biomaterial when, for example, heat generation is itself uniform throughout and no heat transfer is occurring at the boundary—e.g., in an insulated container. One way of attempting to achieve uniform heat generation involves microwave rewarming (e.g., Wusteman et al. *Cryobiology* 48(2):179-189, 2004; Han et al. *Microwave and Optical Technology Letters* 46(3):201-205, 2005). These high frequency fields cannot be applied uniformly within bulk systems, resulting in "hot spots" due at least in part to skin effects, attenuation of the field, and/or variations in the temperature-dependent dielectric constants within the sample. The resulting non-uniformity in thawing can lead to thermal stresses within the frozen sample that can produce cracking and differential viability, fundamentally limiting its applicability. In short, volumetric heating of bulk tissue systems has been explored for more than 30 years, but these fundamental limitations have not been overcome.

Magnetic nanoparticle RF heating can circumvent the issues in microwave warming. Although previous attempts using microwave (100 s of MHz to GHz) thawing have produced heating rates up to hundreds of ° C./min, they also demonstrate the inherent limitation to heating at these high frequency fields in biomaterials, which is non-uniformity. More specifically, microwave heating at high frequencies is due to dielectric coupling of the field with polar molecules. Although this is an effective means to deposit energy into biomaterials with high water content, inhomogeneity will occur even with the use of uniform fields due to variations in the dielectric properties, attenuation of the field (e.g., caused by skin depth), and/or the shape of the sample (Evans S. *Cryobiology* 40(2):126-138, 2000; Burdette E C, Karow A M. *Cryobiology* 15(2):142-151, 1978; Burdette et al. *Cryobiology* 17(4):393-402, 1980; Robinson et al. *Phys. Med. Biol.* 47(13):2311-2325, 2002). This can result in hot spots forming, which are then compounded by "thermal runaway," where the local heating accentuates the mismatch in the temperature-dependent dielectric properties.

However, at lower radiofrequencies (<1 MHz), alternating magnetic fields (AMFs) can uniformly penetrate biomaterials without attenuation and negligible dielectric coupling (Atkinson et al. *IEEE Trans on Biomedical Engineering* 31(1):70-75, 1984). Coupling through induction of non-uniform Eddy currents may still occur, but these are not typically significant given the low electrical conductivities of vitrified solutions. Although these low frequency fields are typically unable to rapidly heat biomaterial on their own, they are able to produce significant losses in distributed magnetic nanoparticles. The mechanisms of heating for magnetic nanoparticles under an AMF may differ based on the particles' magnetic behavior. Superparamagnetic nanoparticles (single-domain crystals typically less than 20 nm)

only exhibit magnetization under an applied magnetic field. Under these conditions they may heat due to Neelian (i.e., individual atomic moment relaxation) and Brownian (i.e., physical particle rotation) mechanisms (Etheridge M L, Bischof J C. *Ann. Biomed. Eng.* 41(1):78-88, 2013; Jordan et al. *International Journal of Hyperthermia* 9(1):51-68, 1993; Rosensweig R E. *Journal of Magnetism and Magnetic Materials* 252:370-374, 2002). On the other hand, larger mNPs are able to maintain remnant magnetization in the absence of an applied field (ferro- or ferrimagnetic behavior) and can heat through hysteresis behavior. Although the physical mechanisms differ, the dynamic heating process for magnetic nanoparticles is described by:

$$u''' = SAR_v = [\pi \ \mu_0 \ f \ H^2] * \chi'' \tag{2}$$

where $SAR_V$ is the heating in a nanoparticle loaded volume, $\mu_0$ is the permeability of free space, f is the applied frequency, H is the applied field strength and $\chi''$ is the out-of-phase component of magnetic susceptibility. This expression can be viewed as two terms—the power density (term in brackets, W/m$^3$) and susceptibility. This essentially represents the incident power and the nanoparticles' efficiency in converting the incident field to heat energy. The incident power is a function of frequency and field strength only, whereas the susceptibility depends strongly on the magnetic nanoparticles' properties, in addition to the suspending environment and applied field. Also, $SAR_V$ can be normalized to the nanoparticle mass ($SAR_{Fe}$, W/mg Fe) ($SAR_V = SAR_{Fe} * [mNP]$). Both embodiments—using superparamagnetic nanoparticles and using ferromagnetic nanoparticles—are reflected in this disclosure.

Figure 5:
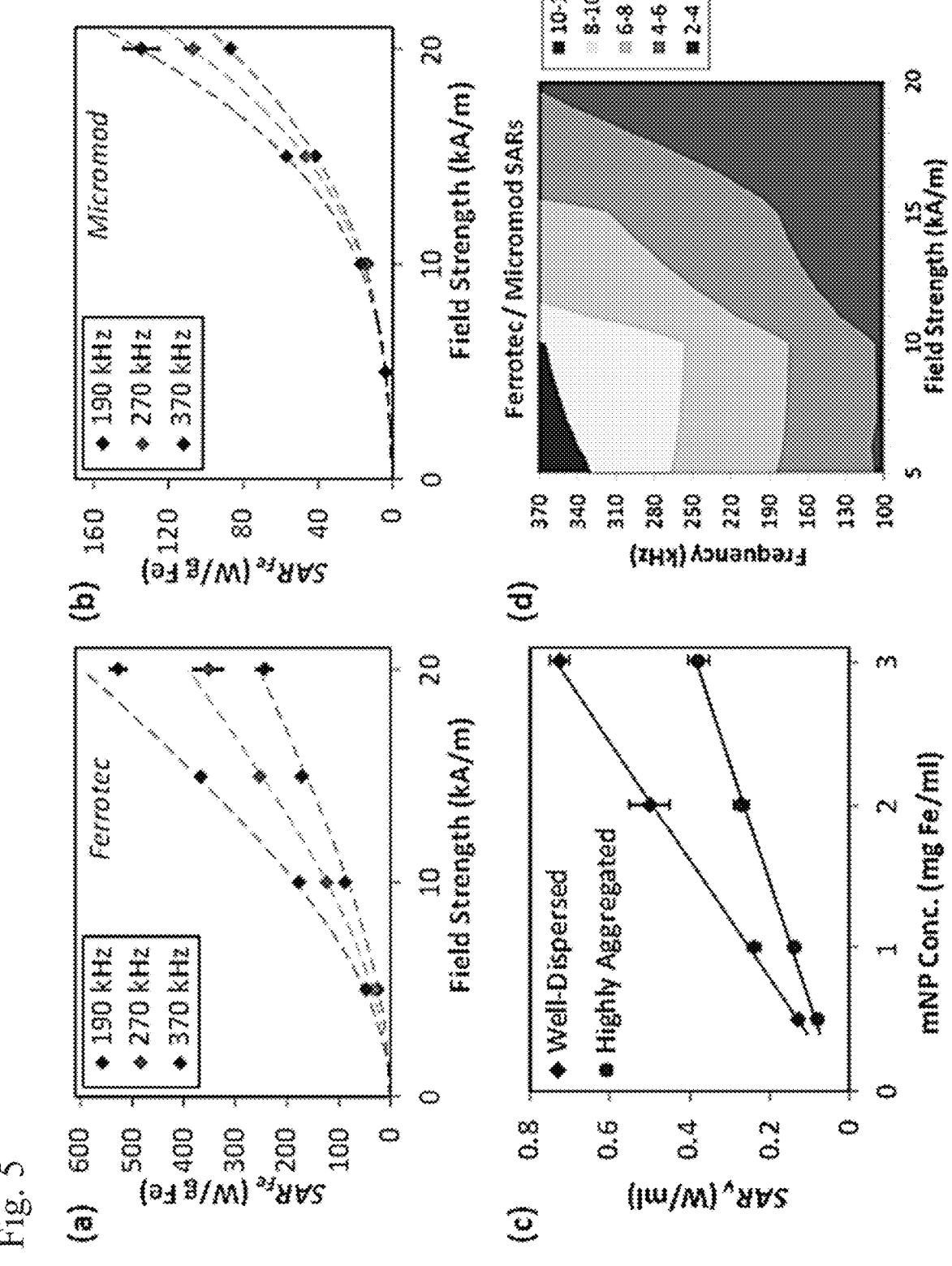
FIG. 5. Mass-normalized, field dependent heating ($SAR_{Fe}$) measured for Ferrotec (superparamagnetic) and Micromod (ferromagnetic) mNPs (a,b) in dispersed, aqueous solution at room temperature. For Ferrotec, the dispersed heating was also compared to a highly aggregated case (destabilized in high concentration phosphate-buffered saline and 1% agarose gel), where an almost 50% drop is observed (c). However, in both cases, the volumetric heating ($SAR_V$) demonstrates a direct dependence on mNP concentration. Importantly, for many field strengths and frequencies tested Ferrotec heats more efficiently on a per nanoparticle basis (2-10-fold as shown) (d).
Figure 6:
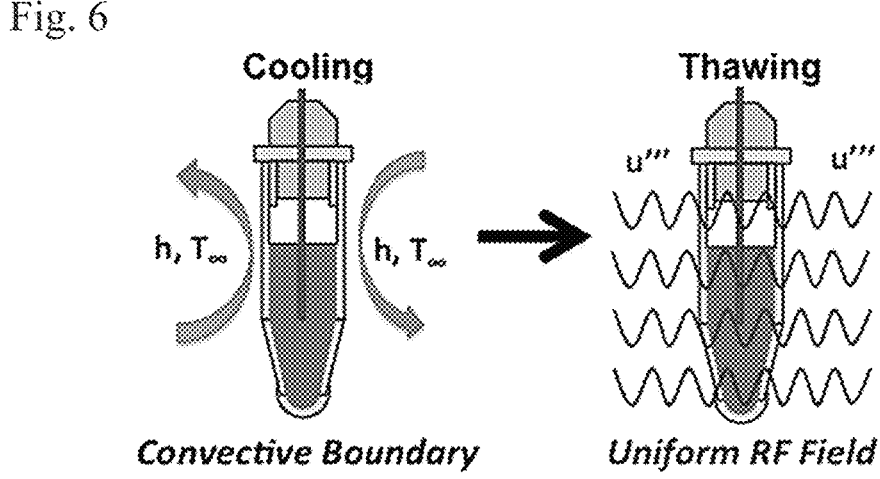
FIG. 6. One mNP cryoprotective agent test bed.

Both fundamental nanoparticle types (superparamagnetic and ferromagnetic) have demonstrated significant levels of heating in the field ranges of interest (FIGS. 5(a) and 5(b)). Referring back to Eqn. 2, the incident power can depend on the square of the applied field and depend directly on the applied frequency. Thus, optimal heating can be achieved at increased field strengths, but the applied field will also affect the magnetic nanoparticles' susceptibility. While the superparamagnetic nanoparticles demonstrate higher heating below 20 kA/m, ferromagnetic nanoparticles may experience significant increases in heating at higher applied fields. FIG. 5(c) shows that magnetic nanoparticle aggregation and confinement can lead to changes in heating behavior (up to a 50% reduction for the superparamagnetic nanoparticles). While ferromagnetic nanoparticles (60-80 nm core, Micromod Partikeltechnologie GmbH, Rostock, Germany) can heat much better on a per nanoparticle basis than superparamagnetic nanoparticles (10 nm core, Ferrotec Corp., Santa Clara, CA) due to their larger volume of iron oxide, the superparamagnetic nanoparticles may heat better on a per mass basis (FIG. 5(d)). This may be important when delivery and distribution of the magnetic nanoparticles within the biomaterial are considered. Finally, magnetic behavior is known to vary with temperature, where a significant increase in magnetization is typically observed at very low temperatures in bulk materials. This trend has also been observed for iron oxide mNPs (43) and may lead to some increase in heating in the cryogenic regime.

Systems capable of applying uniform alternating magnetic fields in the range of interest have been demonstrated and so the uniformity in heating may depend mainly on the magnetic nanoparticle distribution, where volumetric heating is directly proportional to the local magnetic nanoparticle concentration (FIG. 5(c)). One feature of nanoparticles in biomedical applications is their ability to achieve unique biodistributions due the particles' small relative size to that of microscopic tissue structures (Kim et al. *New Eng. J. Med* 2010; 363(25):2434-2443, 2010; Etheridge et al. *Nanomedicine: Nanotechnology, Biology and Medicine* 9(1):1-14, 2013). Biomaterials with larger cavities such as, for example, cardiac chambers or large arteries, also may demonstrate sufficient internal loading and heat transfer that full biomaterial perfusion is not necessary.

The ability to vitrify larger biomaterials typically involves loading the biomaterial with a cryoprotective agent such as, for example, VS55. In order to reduce the critical cooling rates necessary, up to 1000 atm of pressure is used during cooling. Successful thawing in bulk systems after achieving this vitrified state, however, remains a barrier to use of the technology. Specifically, these larger biomaterials can be damaged by devitrification during thawing at suboptimal rates and/or thermal cracking due to non-uniformity of the thaw. Thermal stress can yield cracks, but annealing around the glass transition temperature helps. This idea was subsequently pursued using VS 55 (See Table 1).

To avoid loss of structural integrity, preserved materials must avoid cracking during freezing or thawing. Cracking may be driven by thermal stress and/or strain within the sample. Specifically, when a body sustains changes in temperature and is subjected to tensile stress in a single direction, its strain (deformation) is the sum of these contributions:

$$\varepsilon = \beta \Delta T + \frac{a}{B} \tag{3}$$

where $\varepsilon$ is the strain, $\beta$ is the thermal expansion coefficient, $\Delta T$ is temperature change, $\sigma$ is the stress and E is the Young's modulus. The thermal expansion coefficient has been tabulated for water, tissue components, and various cryoprotective agents in water. The differences in $\beta$ within sub-domains of the tissue, compounded with the temperature changes across a bulk system, can easily create sufficient stress within frozen systems during thawing that lead to cracks (FIG. 1).

This disclosure describes a new approach for rapidly and uniformly heating vitrified biomaterials through the use of radiofrequency-excited magnetic nanoparticles. The addition of magnetic nanoparticles in two well-known cryoprotectants is shown to have negligible effects on their freeze-thaw behavior through differential scanning calorimetry measurements. We then demonstrate the ability of these mNPs to generate heating rates as high 300° C./min, reducing or altogether avoiding devitrification in the vitrified cryoprotectant samples. Finally, the experimentally characterized heating is used to model thawing across several length scales to demonstrate the ability of this approach to provide rapid and uniform heating, independent of sample size or shape.

Two exemplary cryoprotectant solutions were investigated. Glycerol was one of the earliest cryoprotectants studied, but is also considered fairly inefficient by today's standards. Here we look at a 6M mixture of glycerol in 1× phosphate buffered saline (PBS) (hereafter referred to as "6M glycerol"). In contrast, "VS55" is an optimized cryoprotectant cocktail that has demonstrated successful vitrification of many biological systems. VS55 solution is composed of 3.1M dimethyl sulfoxide (DMSO), 2.2M propylene glycol, and 3.1M formamide in a base Euro-Collins solution, for a total of 8.4M. These choices of cryoprotectant solutions should bracket a range of potential behaviors which could be observed for cryoprotectants used in the field. Distilled water is also included as a control reference.

The studies were conducted with commercially available EMG-308 solution (Ferrotec Corp., Santa Clara, CA) composed of $10\pm2.5$ nm-diameter superparamagnetic magnetite ($Fe_3O_4$) nanoparticles coated with an anionic surfactant in aqueous suspension. This system has been previously shown to heat reproducibly, providing a convenient model for study. The stock solution was diluted in the cryoprotectant solutions to provide a concentration of 10 mg Fe/ml. The cryoprotectant-mNP mixtures were formulated to account for the volume of aqueous mNP solution, such that the final mixtures were at 6M glycerol in 1×PBS or 8.4M VS55 in Euro-Collins.

Both 6M glycerol and VS55 solutions have been previously characterized through differential scanning calorimetry (DSC) and some of the important values are summarized in Table 2.

TABLE 2

| Thermal behavior parameters for exemplary cryoprotectant solutions | | |
|---|---|---|
| | 6M Glycerol | VS55 |
| Melt Temperature | −26° C. | −38° C. |
| Glass Transition Temperature | near −100° C. | −123° C. |
| Critical Cooling Rate | −85° C./min | −2.5° C./min |
| Critical Warming Rate | $3.2 \times 10^4$ ° C./min | 50° C./min |

Figure 10:
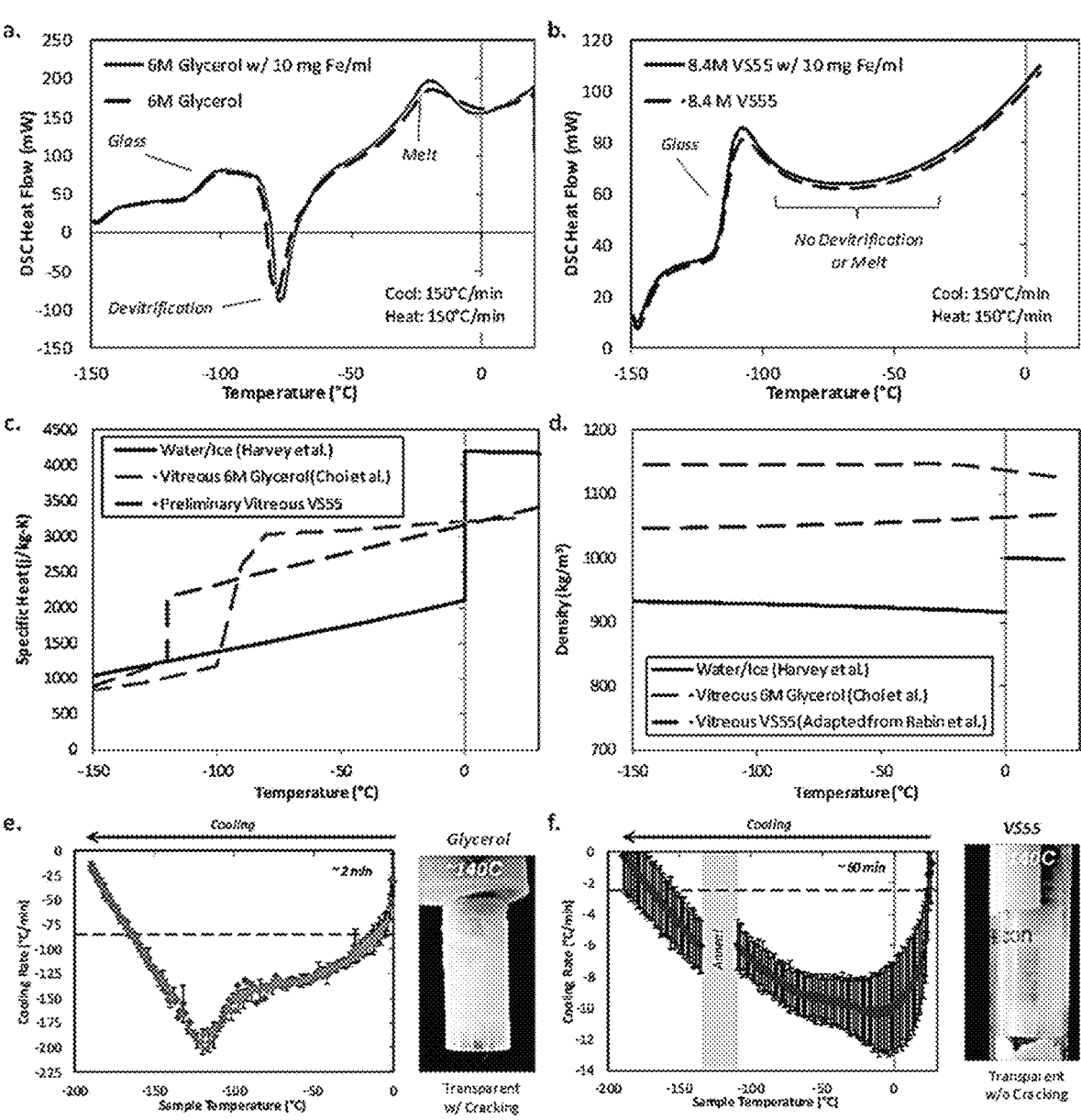
FIG. 10. Freeze-thaw behavior of mNP-cryoprotectant solutions. The addition of nanoparticles in the 6M glycerol and VS55 solutions appeared to have very little impact on the freeze-thaw behavior of the solutions, as demonstrated by the DSC thermal traces for heating at 150° C./min after cooling at −150° C./min (a,b). The specific heat of VS55 was estimated from the apparent specific heat measured by DSC, while the remainder of the thermal property data was estimated, with distilled water included as a standard reference (c, d). Cooling below the critical rate for 6M glycerol required a liquid nitrogen quench and the rapid (non-uniform) cooling resulted in significant cracking in the samples (e). While the VS55 samples were still cooled in a liquid nitrogen bath, several insulating layers provided for a more controlled cooling rate (with an annealing step), allowing the samples to be vitrified and cooled to −192° C. without cracking (f).

FIG. 10(a) and FIG. 10(b) illustrate a thermal trace on heating for the two vitrified solutions, with and without nanoparticles. Two things are apparent. First, the nanoparticles appear to have negligible impact on the freeze-thaw behavior of the solutions—i.e., the mNPs do not produce a significant shift in the phase transitions experienced by each solution. Differences between the two solutions with respect to vitrified behavior are apparent, however. Both solutions experience a glass transition, but the absence of any additional latent heat in the VS55 thermal trace indicates that the solution maintained the amorphous phase without crystallization. In contrast, the 6M glycerol solution experiences a significant heat release during devitrification and latent heat during melting. These heat traces were performed at a heating rate of 150° C./min, which is well above the critical warming rate for VS55. In contrast, heating rates on the order of $10^{4°}$ C./min would be required to avoid devitrification in 6M glycerol. FIG. 10(c) and FIG. 10(d) illustrate the specific heat and densities for 6M glycerol and VS55, based on these DSC studies or literature (Choi, J. H., and J. C. Bischof. *Cryobiology* 57:79-83, 2008; Choi, J. H., and J. C. Bischof. *Int. J. Heat Mass Transf.* 51:640-649, 2008; Harvey, A. H. Properties of Ice and Supercooled Water. In: CRC Handbook of Chemistry and Physics 2012-2013. Boca Raton, FL: CRC Press, 2012, pp. 6-12; Jimenez Rios, J. L., and Y. Rabin. *Cryobiology* 52:269-283, 2006; Rios, J. L. J., and Y. Rabin. *Cryobiology* 52:284-294, 2006). These values will be important in the subsequent analysis and modeling of heating.

Aqueous, 6M glycerol, and VS55 solutions with or without magnetic nanoparticles were heated in a radiofrequency alternating magnetic field (AMF) at 22.8 kA/m (peak, volume-averaged field strength) and 360 kHz (FIG. 11(a)). The cryoprotectant solutions were cooled down to −192° C. at sufficient rates to produce vitrification (FIG. 10(e) and FIG. 10(f)) and then quickly transferred into the inductive coil for immediate heating inside of a sealed plastic vial, to lessen direct losses to the environment (FIG. 11(c)). Fine thermocouples (40-gauge, OMEGA Engineering, Inc., Stamford, CT) were embedded in the samples prior to cooling and provided continuous temperature monitoring in conjunction with a NI-DAQ data acquisition system (National Instruments Corp., Austin, TX). RF fields are expected to produce interference in metallic thermocouples, but this was characterized and found to be negligible in the ultrafine gauge thermocouples used.

The sample temperature data from the control and RF heated samples were used to estimate two values as a function of temperature: the heating rate and the mNP SAR. The sample temperature was acquired at a frequency of 1 Hz, so the heating rate was calculated from the temperature difference between each measurement point, divided by the elapsed time; and the temperature was then taken as the average between those two points. The heating rates (as a function of temperature) for the aqueous, glycerol, and VS55 samples are included in FIG. 11(a-c). While losses to the ambient, room temperature surroundings resulted in some heating in the control samples, the RF field did not induce any additional heating in the samples without nanoparticles. Importantly, however, heating rates on the order of 100s ° C./min were achieved in the mNP-laden samples. These heating rates were high enough to significantly reduce devitrification in the glycerol samples (FIG. 11(b)) and avoid it in the case of VS55 (FIG. 11(c)).

To better understand IONP heating for this application, SAR was also estimated from an energy balance on the samples, following[11]:

$$c_p(T_s)\rho(T_s) * \frac{dT}{dt}(T_s) = hA(T_s) * (T_s - T_a) + SAR_V(T_s) \tag{4}$$

where $T_s$ is the sample temperature ($f(T_s)$ indicates a function of sample temperature), $c_p$ and $\rho$ are the specific heat and density of the solution, dT/dt is the measured heating rate, hA is an estimated ambient loss coefficient, $T_a$ is the ambient room temperature, and $SAR_V$ is the volumetric heating due to the IONPs (equivalent to q''' in a typical energy balance). The ambient loss coefficient was estimated from the control samples by assuming $SAR_V=0$ and solving for hA at each sample temperature. The $SAR_V$ could then be estimated for each radiofrequency heating case, as a function of sample temperature. The estimated SAR for a number of cases is compared in FIG. 12(a-c).

Without wishing to be bound by any particular theory, these results can be explained by three factors: (1) IONP aggregation, (2) suspending phase, and/or (3) material magnetization. First, aggregation and confinement can lead to reductions in heating at room temperature for the magnetic nanoparticles studied. Significant aggregation was visually observed on mixing of the magnetic nanoparticles with the VS55 solution and this accounts for the drop in heating observed for the room temperature VS55 suspensions (FIG. 12(b)). However, if one concentrates on the phase transitions encountered during heating (FIG. 12(c), the solid-liquid transition in the aqueous sample and the glass transition in the glycerol and VS55 samples), it appears the IONPs heat less efficiently in the more rigid phases. The IONPs heat nearly 70% less in −5° C. crystalline ice than they do suspended in liquid water at room temperature. And while not as significant, there also appears to be a reduction in heating observed between the glass and liquid phases in glycerol. Finally, IONP magnetization can influence heating, with significant heating increases correlating with increases in material magnetization. (Hergt et al. *Magn. IEEE Trans. On* 34:3745-3754, 1998; Rosensweig, R. E. *J. Magn. Magn. Mater.* 252:370-374, 2002). It is also common for the magnetization of materials to increase at lower temperatures and this has been shown to hold true for iron oxide nanoparticles. (O'Handley, R. C. Modern magnetic materials: principles and applications. New York, NY: Wiley, 2000, 740 pp.; Roca et al. *Nanotechnology* 17:2783, 2006) This may cause the increasing trend in heating observed at lowering temperatures observed in some of the phases (FIG. 11($d$)).

Figure 12:
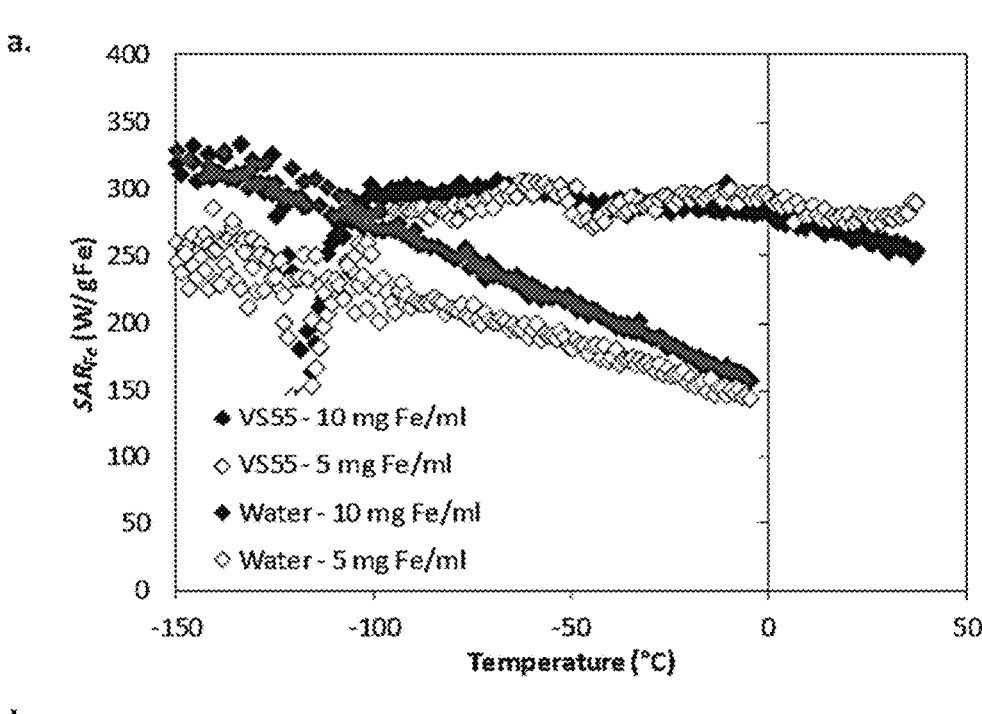
FIG. 12. SAR for mNPs heating in the cryogenic regime. Analysis of the heating data provided estimates of the SAR as a function of temperature, demonstrating very complex behavior (a-c). The observed heating may reflect the effects of nanoparticle aggregation (b), suspending phase (c), and temperature-dependent magnetic behavior (a).
Figure 12:
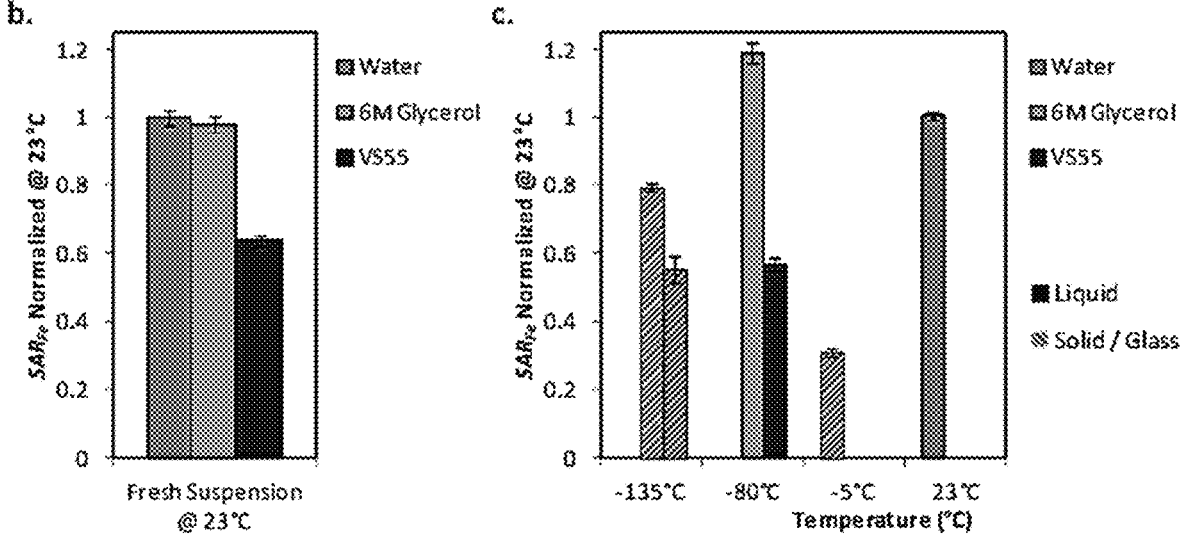

One phenomenon observed for the crystallized ice and glassy VS55 phases is the apparent increase in $SAR_{Fe}$ for the 10 mg Fe/ml case over the 5 mg Fe/ml case (FIG. 12($a$)). In the absence of interparticle interactions, $SAR_{Fe}$ is expected to be independent of magnetic nanoparticle concentration. However, the increase in $SAR_{Fe}$ with increased magnetic nanoparticle concentration might suggest an inverse trend to the aggregation effects observed at room temperature. Thus, the interacting effects of aggregation, structure of the suspending phase, and/or temperature-dependent magnetic behavior may be quite complicated.

COMSOL MULTIPHYSICS (COMSOL Inc., Burlington, MA) was used to compare the case of uniform volumetric heating to convective boundary warming. A cylindrical volume was chosen as a representative case. While this is a rather generic geometry, these results are generally applicable to a wide range of tissue systems. While organ geometries can vary, cryopreservation protocols are typically performed with the organ submersed in a volume of cryoprotectant held in a container, which is often cylindrical (FIG. 13($a$)). The cylindrical volume was simulated by a 2D axisymmetric case where the height was equal to two times the radius. This radius was scaled from 0.2 cm to 3 cm to demonstrate the effects of sample size on heating. Two heating cases were compared in a transient, conductive heat transfer simulation.

For the traditional warming case, a convective heat transfer coefficient of h=25 W/m²-K and ambient temperature of $T_a$=37° C. were applied to the boundary of the simulated volume, representative of, for example, a hot water bath. For the magnetic nanoparticle thaw case, it was assumed that the boundaries of the volume were insulated (adiabatic, ∂T/∂n=0), but that a uniform heat generation rate (q'''=$SAR_V$) was applied throughout the volume. $SAR_V$ was applied based on the data in FIG. 11 for concentrations of 5 mg Fe/ml or 10 mg Fe/ml ($SAR_V$=$SAR_{Fe}$ X [Fe]). In all cases, the volume was initially assumed to be at −196° C. and the temperature-dependent specific heat and density were applied as interpolation functions, based on the data for VS55 in FIG. 10. The default "Extremely Fine" mesh settings were used and the number of elements depended on the size of the volume simulated. The default transient solver conditions were used.

Figure 13:
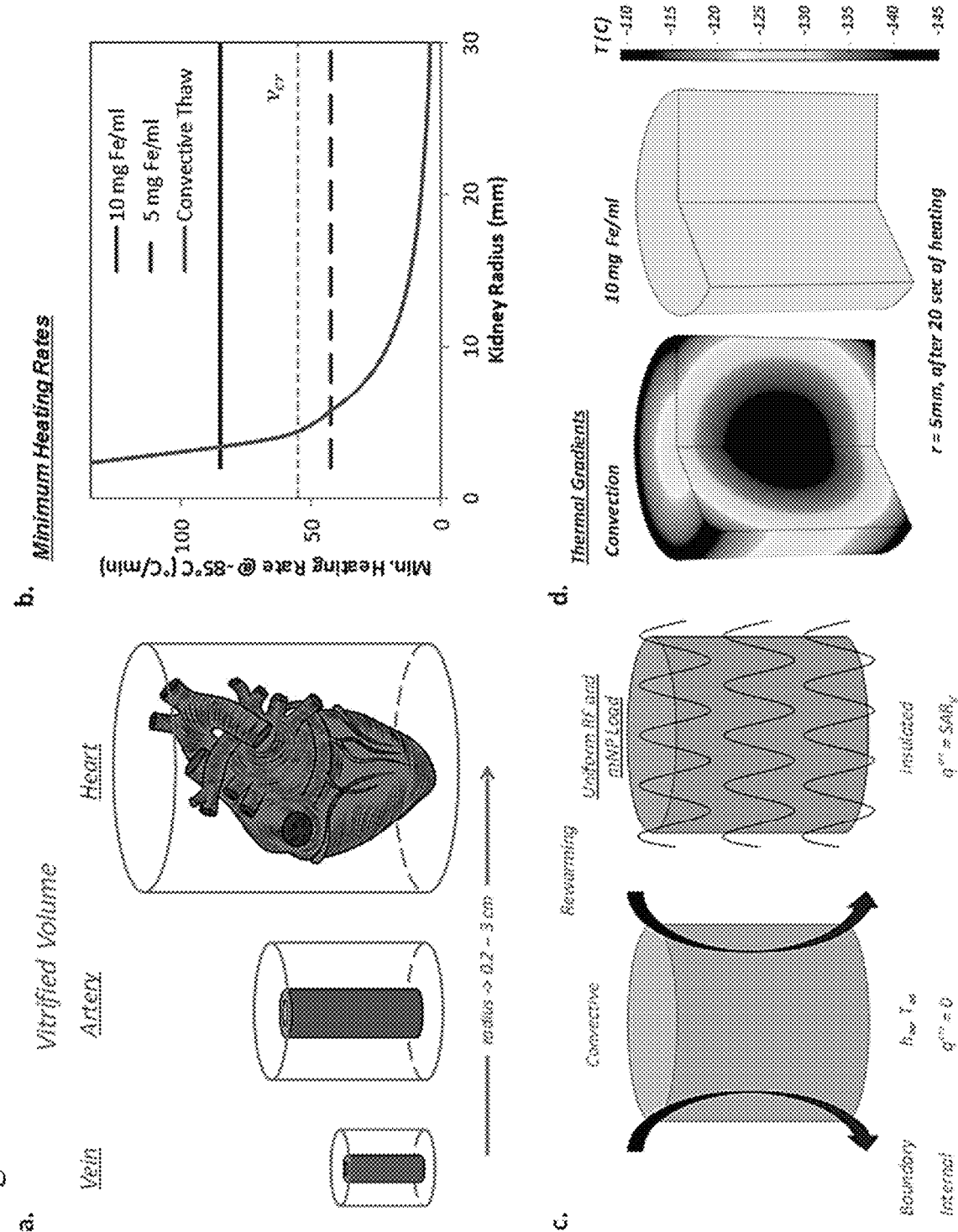
FIG. 13. Modeling uniform radiofrequency heating of mNPs in bulk vitrified biomaterials. While tissues and organs can feature a variety of complex geometries, vitrification protocols will typically involve submersion and cooling in more simplified geometries. Here we compared the general case of a vitrified cylindrical volume, which can apply to a broad spectrum of cryopreservation applications (a). The cases of convective, boundary warming and uniform heating generation (c) were compared for a range of characteristic dimensions and the calculated minimum heating rate (b) demonstrates the independence of this technique on sample size. The thermal gradients which result from boundary warming are also quite apparent for the convective case (d).

A parametric study was used to solve each warming case for cylindrical radii varying from 0.2 cm to 3 cm (in 0.2 cm increments) and the minimum warming rates were compared. The greatest risk of devitrification is around −85° C. (Mehl, P. M. *Cryobiology* 30:509-518, 1993; Rabin et al. *Cell Preserv. Technol.* 3:169-183, 2005) and, based on diffusive mechanisms, the slowest warming rate is typically at the center of the sample. Therefore, the minimum warming rates are compared for the spatial and temporal point when the center of the sample reaches −85° C. The calculated minimum warming rates are illustrated in FIG. 13($b$). While convective warming is able to produce fairly high rates for radii dimensions on the order of 1 mm, the warming rates are slowed dramatically for geometries that have a radius greater than about 5 mm. In contrast, the uniform heat generation for the magnetic nanoparticle thaw case is independent of sample size (and shape), providing for rapid heating rates even in bulk samples. The other benefit of uniform heat generation is illustrated in FIG. 13($d$). While a uniform temperature field is demonstrated for the magnetic nanoparticle thaw case, significant temperature gradients exist for the convective case, which can produce thermal stresses.

The idealized case of uniform heat generation implies a sufficiently uniform distribution of nanoparticles. However, there are many cases where the magnetic nanoparticle distribution may not be perfectly uniform. To investigate the application's sensitivity to non-uniform particle distribution, we looked at a one-dimensional planar case (FIG. 14($a$)) where a section of tissue with thickness L without heat generation is contained within a semi-infinite medium subjected to a heat generation term ($SAR_V$). This case is analogous to an unloaded thin tissue being submersed in a mNP-cryoprotectant solution or incomplete perfusion of magnetic nanoparticles within a cryoprotectant-loaded bulk tissue. Symmetry was applied along the tissue's centerline and semi-infinite behavior was approximated by simulating the domain out to 50×L, where an adiabatic boundary was applied. The transient heat equation was then solved in MATHEMATICA (Wolfram Research, Inc., Champaign, IL), for thicknesses ranging between 1 mm and 15 mm. The $SAR_V$ was calculated as above for a magnetic nanoparticle concentration of 10 mg Fe/ml and the temperature-dependent specific heat and density were input from an interpolation function based on the data in FIG. 10.

The minimum heating rates were again calculated for each case when the center reached −85° C. In addition, since the heat generation was no longer uniform, the imposed temperature gradients produce thermal stress in the biomaterial. This was approximated based on a modification to the "thermal shock" equation, following:

$$\sigma_T = g*\left(\frac{E\beta\Delta T}{1-v}\right) \tag{5}$$

(Manson, S. S. *NACA Rep.* 1170:317-350, 1954; Steif et al. *Cell Preserv. Technol.* 5:104-115, 2007) where $\sigma_T$ is the thermal stress, g is a geometric coefficient (estimated as 0.33), E is the modulus of elasticity (estimated as 1 GPa), $\beta$ is the coefficient of thermal expansion (calculated as a function of temperature based on data in Jimenez et al. *Cryobiology* 52:269-283, 2006), $\Delta T$ is the maximum temperature difference in the material, and v is Poisson's ratio (estimated as 0.2). The greatest risk of fracture is generally around the glass transition temperature, below which elastic behavior dominates. Thus, the thermal stress analysis focused on temperatures below about −123° C. Above this point, the viscosity begins to decrease dramatically and so nucleation becomes a significant challenge.

Significant additional thermal stresses induced during cooling can exist in the vitrified biomaterial, but these are a product of the cooling protocol and the current analysis is focused on rewarming. More detailed thermal stress analyses can account for thermal stress that results from cooling, but the stresses calculated in Equation (5) should be viewed as an additional thermal stress that results from rewarming the vitrified material.

Figure 14:
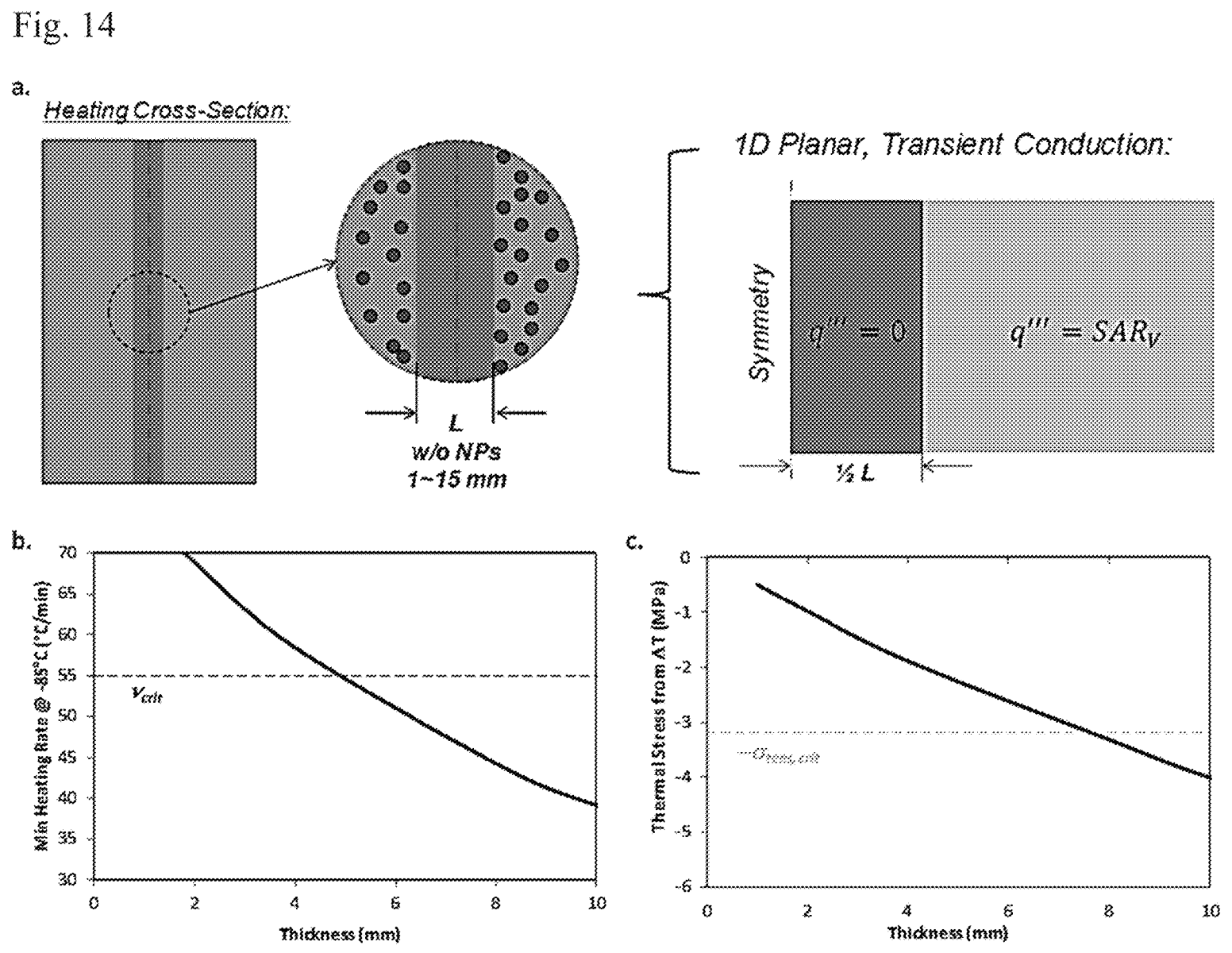

The minimum heating rate and thermal stress approximations as a function of unloaded thickness (L) are included in FIG. 14(*b*) and FIG. 14(*c*). While the non-uniformity in heating induces some thermal stress, the material is expands upon heating and these stresses will be compressive, so the magnitude of stress experienced is reduced to acceptable levels. In contrast, the minimum heating rate again appears to be the limiting factor. For thicknesses above about 5 mm, the heating rate at the centerline drops below the critical warming rate and some devitrification can occur. The 5 mm thickness threshold is large enough, however, to accommodate many thin tissues such as, for example, luminal tissues (e.g., veins and arteries) that are typically smaller than 5 mm in thickness. The 5 mm thickness threshold also assumes a worst case loading. Rewarming protocols generally can allow equilibration with not only the cryoprotectant, but allow distribution of magnetic nanoparticles as well, so these limitations will be relaxed further as the magnetic nanoparticles permeate even partially into the tissue.

The present study provides data and modeling in support of a new approach for magnetic nanoparticle thawing of cryopreserved tissues. The use of magnetic nanoparticles for rewarming a cryopreserved biospecimen can provide faster, more uniform heating rates that can, in turn, reduce devitrification and/or other detrimental effects on cryopreserved biospecimens. Further, the use of magnetic nanoparticle to rewarm a cryopreserved biospecimen may facilitate cryopreservation of larger systems with lower molarity cryoprotectants, thereby reducing toxicity issues. In addition, it is known that magnetic nanoparticle design and the applied RF field are factors in the level of heating achieved. The magnetic nanoparticles studied demonstrated complex behavior while heating in the cryogenic regime. Finally, the basic experiments in cryoprotectant solutions can be expanded to include study of the impact on biological systems, including cellular suspensions and simple tissue systems. This will include a characterization of heating in these systems, as well as the effects on viability, structure, and function.

Thus, in one aspect, this disclosure describes a cryoprotective composition that includes a cryoprotective agent and magnetic nanoparticles effective for thawing a cryopreserved specimen that includes biomaterial with minimal damage to the biomaterial. The cryoprotective agent can include any material suitable for the cryopreservation of biomaterials. Exemplary suitable cryoprotective agents include, for example, combinations of alcohols, sugars, polymers and ice blocking molecules that alter the phase diagram of water and allow a glass to be formed more easily (and/or at higher temperatures) while also reducing the likelihood of ice nucleation and growth during cooling or thawing. In most cases, cryopreservative agents are not used alone, but in cocktails. In the case of vitrification solutions, exemplary cryopreservative cocktails are reviewed in Fahy et al. *Cryobiology* 48(1):22-35, 2004.

In some embodiments, the cryoprotective agent may be present in the composition at a molarity of no more the 6 M such as, for example, no more than 5 M, no more than 4 M, no more than 3 M, no more than 2 M, no more than 1 M, no more than 900 mM, no more than 800 mM, no more than 700 mM, no more than 600 mM, no more than 500 mM, or no more than 250 mM.

The magnetic nanoparticles may be any magnetic nanoparticles excitable by a radio frequency (i.e., RF susceptible nanoparticles), including, without limitation, alternating magnetic frequencies, or rotating magnetic frequencies, and as described below. The magnetic nanoparticles can include one or more magnetic elements such as, for example, iron, nickel and/or cobalt, and compounds containing one or more atoms of a magnetic element. As used herein, a particle may be considered a nanoparticle if it possesses a maximum diameter of no more than one micrometer (μm), but may be incorporated as part of a structure—e.g., an aggregate—with characteristic dimensions larger than one micrometer. The dimensions provided herein refer to dimensions of the nanoparticle, not the dimension of the larger structure. Thus, the maximum diameter of a nanoparticle can be, for example, no more than 800 nanometers (nm), no more than 700 nm, no more than 600 nm, no more than 500 nm, no more than 450 nm, no more than 400 nm, no more than 350 nm, no more than 300 nm, no more than 250 nm, no more than 200 nm, no more than 150 nm, no more than 100 nm, no more than 90 nm, no more than 80 nm, no more than 70 nm, no more than 60 nm, no more than 50 nm, no more than 40 nm, no more than 30 nm, no more than 25 nm, no more than 20 nm, no more than 15 nm, or no more than 10 nm. A particle can be considered a nanoparticle if it possesses a minimum diameter of at least 1 nm such as, for example, at least 2 nm, at least 3 nm, at least 4 nm, at least 5 nm, at least 6 nm, at least 7 nm, at least 8 nm, at least 9 nm, at least 10 nm, at least 25 nm, at least 50 nm, at least 100 nm, at least 250 nm, or at least 500 nm. In some embodiments, the size of the magnetic nanoparticles may include a range with endpoints defined by any maximum diameter listed above and any minimum diameter listed above that is smaller than the maximum diameter.

In some embodiments, the magnetic nanoparticles can include superparamagnetic nanoparticles. In other embodiments, the magnetic nanoparticles can include ferromagnetic nanoparticles. The nanoparticles can have any suitable shape such as, for example, spherical, cubical, pyramidal, etc. In some embodiments, the magnetic nanoparticles can include a combination of any two or more types of magnetic nanoparticles. In some embodiments, as noted briefly above, the magnetic nanoparticles can aggregate. In such embodiments, the magnetic nanoparticles can interact with one another. In some of these embodiments, one can tune the aggregation of nanoparticles to enhance or diminish the heating rate in a particular application, as desired.

The magnetic nanoparticles can be present in the cryoprotective composition in an amount sufficient to provide minimum at least 0.01 mg of magnetic atoms per milliliter of the vitrified tissue such as, for example, at least 1.0 mg/ml, at least 2.0 mg/ml, at least 3.0 mg/ml, at least 4.0 mg/ml, at least 5.0 mg/ml, at least 6.0 mg/ml, at least 7.0 mg/ml, at least 8.0 mg/ml, at least 9.0 mg/ml, at least 10 mg/ml, at least 11 mg/ml, at least 12 mg/ml, at least 13 mg/ml, at least 14 mg/ml, at least 15 mg/ml, at least 20 mg/ml, at least 25 mg/ml, or at least 50 mg/ml. In some embodiments, the magnetic nanoparticles can be present in the cryoprotective composition in an amount sufficient to provide a maximum of no more than 100 mg/ml, no more than 75 mg/ml, no more than 50 mg/ml, no more than 25 mg/ml, no more than 20 mg/ml, no more than 15 mg/ml, no more than 10 mg/ml, no more than 9 mg/ml, no more than 8 mg/ml, no more than 7 mg/ml, no more than 6 mg/ml, or no more than 5 mg/ml. In some embodiments, the amount of the magnetic nanoparticles in the cryoprotective composition may be characterized as a range having endpoints defined by any minimum amount listed above and any maximum amount listed above that is smaller than the maximum amount.

The cryoprotective composition can be used in a method for thawing a cryopreserved specimen that includes bioma- terial with minimal damage to the biomaterial. As used herein, "cryopreserved" refers to a biomaterial—e.g., a tissue sample, organ, portion of an organ, cell suspension, or cell monolayer—that has been perfused with or suspended in a cryoprotective composition as described herein and cooled as described in more detail below.

Also as used herein, "minimal damage" refers to an amount of damage to the thawed biomaterial insubstantial enough so that the biomaterial retains its desired biofunc- tionality when thawed. Thus, minimal devitrification can allow for some degree of damage and the permissible amount may vary depending upon the intended use of the biomaterial after thawing. In this context, "damage" is a collective term that generically refers to damage to bioma- terial that can commonly result in failed cryopreservation. Such damage includes, for example, devitrification and/or cracking. In embodiments in which the biomaterial includes, for example, an organ for transplantation, the thawed organ having "minimal damage" may sustain some damage, but remains useful for transplantation into a recipient. As another example, in embodiments in which the biomaterial includes, for example, reproductive materials (e.g., ova, sperm, semen), the specimen having "minimal damage" may include an acceptable percentage of non-viable cells while retaining a useful percentage of viable cells.

In some embodiments, the cryopreserved biomaterial can include biomaterial perfused with or suspended in a volume of the cryoprotective composition having a smallest linear dimension of 0.1 mm. In some embodiments, the smallest linear dimension can be, for example, at least 0.1 mm, at least 0.5 mm, at least 1 mm, at least 2 mm, at least 5 mm, at least 1 cm, at least 2 cm, at least 5 cm, at least 10 cm, at least 25 cm, at least 50 cm, or at least 100 cm. In the embodiments in which the biomaterial is perfused with the cryoprotective composition, the dimension listed above may be, in effect, the dimension of the biomaterial. In embodi- ments in which the biomaterial is suspended in a cryopro- tective composition, the dimension may reflect a vessel containing the cryopreserved biomaterial and/or a vessel in which the cryopreserved biomaterial was cooled.

In another aspect, this disclosure describes a biomaterial such as, for example, an organ or a portion thereof that is perfused with or suspended in a cryoprotective composition as described herein. The perfused and/or suspended bioma- terial may be vitrified or thawed.

In another aspect, this disclosure describes a method of cryopreserving a biomaterial. Generally, the method includes with a cryoprotective composition as described herein and cooling the perfused biomaterial to a suitable cryopreservative temperature. Suitable cryopreservative temperatures can include, for example, a temperature below the glass transition temperature of the cryoprotective agent in the cryoprotective composition. As one example, the glass transition temperature of 6 M glycerol is −100° C. Accord- ingly, the biomaterial may be cooled to a maximum tem- perature of no more than 0° C. such as, for example, no more than −20° C., no more than −40° C., no more than −80° C., no more than −100° C., no more than −120° C., no more than −130° C., no more than −140° C., no more than −150° C., no more than −160° C., no more than −170° C., no more than −180° C., no more than −190° C., or no more than −200° C. In some embodiments, suitable cryopreservative temperatures can include a minimum temperature of no less than −220° C., no less than −200° C., or no less than −150° C. In some embodiments, suitable cryopreservative temperatures can be characterized as a range having as endpoints any maximum temperature listed above and any minimum tem- perature listed above that is less than the maximum tem- perature. In some embodiments, a suitable cryopreservative temperature may be the boiling point of nitrogen, −196° C. Our approach is particularly useful in cryoprotective sys- tems where the glass transition is below 0° C., when biomaterial may be subject to devitrification during thawing.

The perfused biomaterial may be cooled to the cryo- preservative temperature at a rate effective for cryopreser- vation. Cooling rates can promote vitrification of the per- fused biomaterial. In some embodiments, the perfused biomaterial may be cooled at a minimum rate of at least 1° C. per minute (° C./min) such as, for example, at least 2° C./min, at least 5° C./min, at least 10° C./min, at least 15° C./min, at least 20° C./min, at least 25° C./min, at least 30° C./min, at least 40° C./min, at least 50° C./min, at least 60° C./min, at least 70° C./min, at least 100° C./min, at least 1000° C./min, or multiple thousands ° C./min. In some embodiments, the perfused biomaterial may be cooled at a maximum rate of no more than 100° C./min such as, for example, no more than 80° C./min, no more than 60° C./min, no more than 50° C./min, no more than 40° C./min, no more than 30° C./min, or no more than 20° C./min. In some embodiments, the cooling rate may be within a range of cooling rate having endpoints defined by any minimum cooling rate listed above and any maximum cooling rate listed above that is greater than the minimum cooling rate. In embodiments involving larger systems, the cooling pro- cess can involve use of a high pressure freezing vial as described by Fahy et al. *Cryobiology* 48(2):157-178, 2004. Added pressure—e.g., up to 1000 atm—can reduce the ability of ice to nucleate and grow within the sample during cooling. However, samples cooled in this manner can require rapid thawing to avoid devitrification and cracking.

In yet another aspect, this disclosure describes a method of thawing a cryopreserved biomaterial. Generally, the method includes obtaining a biomaterial cryopreserved with a cryopreservative composition as described herein, and subjecting the cryopreserved biomaterial to electromagnetic energy of an intensity, and for a duration, effective to thaw the biomaterial. In some embodiments, the biomaterial may exhibit minimal devitrification, as defined herein, while being thawed.

In some embodiments, the electromagnetic energy can include a radio frequency field, alternating magnetic field, or rotating magnetic field. In such embodiments, the electro- magnetic energy can exhibit a minimum frequency of no more than 1 MHz such as, for example, no more than 750 kHz, no more than 500 kHz, no more than 375 kHz, no more than 300 kHz, no more than 250 kHz, no more than 225 kHz, no more than 200 kHz, no more than 175 kHz, no more than 150 kHz, no more than 125 kHz, no more than 100 kHz, no more than 75 kHz, or no more than 50 kHz. In some embodiments, the radio frequency field can exhibit a maxi- mum frequency of at least 1 kHz such as, for example, at least 5 kHz, at least 10 kHz, at least 25 kHz, at least 50 kHz, at least 75 kHz, at least 100 kHz, at least 125 kHz, at least 150 kHz, at least 175 kHz, at least 200 kHz, at least 225 kHz, or at least 250 kHz. In some embodiments, the radio frequency field may be characterized by a range of frequen- cies having as endpoints any minimum frequency listed above and any maximum frequency listed above that is greater than the minimum frequency and may be time-dependent. In some embodiments, for example, the radio frequency field may range from about 175 kHz to about 375 kHz. In another particular example, the radio frequency field may range from 100 kHz to about 500 kHz.

In some embodiments, the radio frequency field may have a minimum strength of at least 1 kA/m such as, for example, at least 5 kA/m, at least 10 kA/m, at least 20 kA/m, at least 30 kA/m, at least 50 kA/m, at least 75 kA/m, or at least 100 kA/m. In some embodiments, the radio frequency filed may have a maximum strength of no more than 200 kA/m such as, for example, no more than 150 kA/m, no more than 100 kA/m, no more than 80 kA/m, no more than 50 kA/m, or no more than 25 kA/m. In some embodiments, the strength of the radio frequency field may be characterized as a range having as endpoints any minimum strength listed above and any maximum strength listed above that is greater than the minimum strength and may be time-dependent. In some embodiments, the radio frequency field may have a strength of from about 10 kA/m to about 100 kA/m. In one particular embodiment, the radio frequency filed can have a strength of 24 kA/m.

In some embodiments, the biomaterial may be warmed at a minimum rate of at least 50° C./min such as, for example, at least 75° C./min, at least 100° C./min, at least 125° C./min, at least 150° C./min, at least 175° C./min, at least 200° C./min, at least 225° C./min, at least 250° C./min, at least 275° C./min, or at least 300° C./min. In some embodiments, the biomaterial may be warmed at a maximum rate of no more than 100,000° C./min such as, for example, no more than 1500° C./min, no more than 1000° C./min, no more than 750° C./min, no more than 500° C./min, no more than 400° C./min, no more than 300° C./min, no more than 250° C./min, no more than 200° C./min, no more than 175° C./min, or no more than 150° C./min. In some embodiments, the biomaterial may be warmed at a rate within a range having endpoints defined by any minimum rate listed above and any maximum rate listed above that is greater than the minimum rate. In certain embodiments, the biomaterial may be warmed at a rate of about 300° C./min. In other particular embodiments, the biomaterial may be warmed at a rate of about 225° C./min or about 175° C./min.

In some embodiments, the biomaterial may be warmed at a constant rate throughout the biomaterial according to Equation (1), above. As used herein, "constant rate throughout the biomaterial" refers to a temperature gradient of no more than 1° C./m across the biomaterial such as, for example, no more than 1° C./cm across the biomaterial or no more than 1° C./mm across the biomaterial.

In the preceding description, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

Also in the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

Compositions and methods are illustrated by the preceding description. It is to be understood that the particular examples, materials, amounts, and procedures are to be interpreted broadly in accordance with the scope and spirit of the invention as set forth herein.

EXAMPLES

Differential Scanning Calorimetry Methods

The freeze-thaw behavior of 6M glycerol (Sigma-Aldrich, St. Louis, MO) and VS55 (Rall W F, Fahy G M. *Nature* 313(6003):573-575, 1985), both with and without the addition of 10 mg Fe/ml nanoparticles, was measured with a Diamond differential scanning calorimeter (PerkinElmer Inc., Waltham, MA) from −150° C. to 25° C. Ten milligram samples were placed in aluminum sample pans. Water, sapphire, and an empty sample pan were used as calibration standards during each day of measurements. All experimental measurements were repeated for n=3. The samples were cooled at −150° C./min to ensure complete vitrification of the cryoprotectant samples.

Various warming rates were included in the preliminary investigations (5° C./min, 20° C./min, 50° C./min, 100° C./min, and 150° C./min) to verify previously observed freeze-thaw behaviors—i.e., phase transitions and critical warming rates. The heat flows for heating rate and cooling rate were calibrated for cyclohexane and n-decane. The DSC protocols (Choi, J., and J. C. Bischof. *Cryobiology* 60:52-70, 2010; Choi, J. H., and J. C. Bischof. *Cryobiology* 57:79-83, 2008; Choi, J. H., and J. C. Bischof. *Int. J. Heat Mass Transf.* 51:640-649, 2008) included two-minute hold times at the end-point temperatures between each ramping period. The specific heat for VS55 was characterized between −150° C. and 25° C. for a heating rate of 50° C./min. The specific heats of pure water/ice and pure glycerol also were measured following the same protocol, to provide quantitative reference standards. The measurement protocol demonstrated good agreement for both standards.

Figure 15:
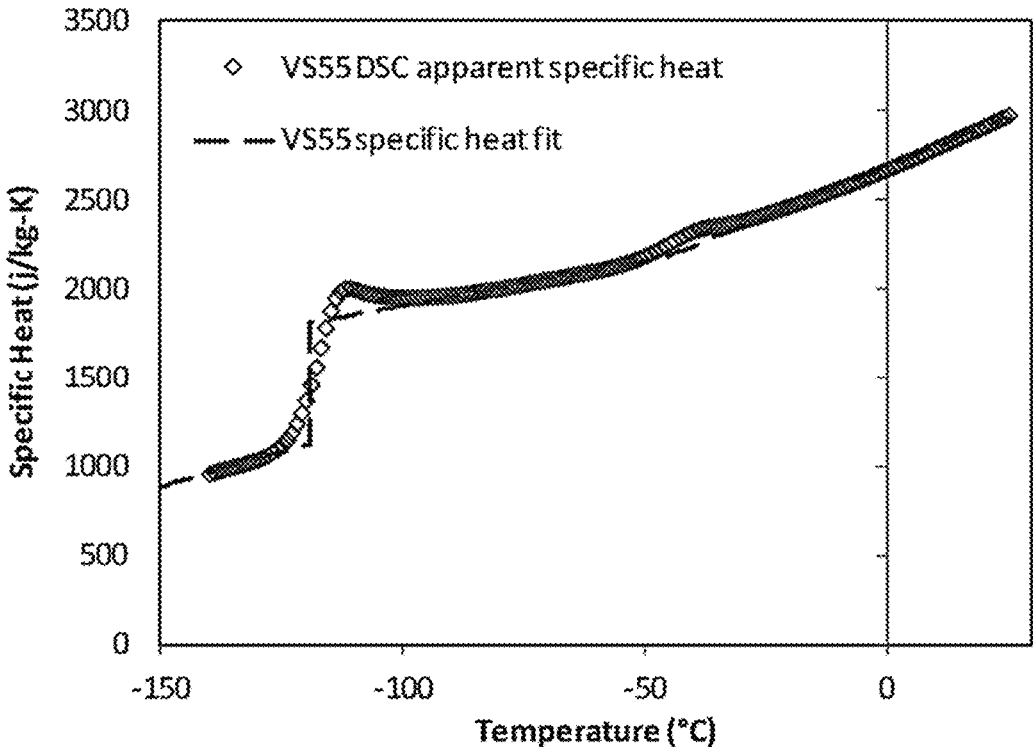
FIG. 15. Estimation of baseline specific heat for VS55. The baseline specific heat of VS55 was extracted from the measured apparent specific heat as previously described in Choi, J., and J. C. Bischof. *Cryobiology* 60:52-70, 2010; Choi, J. H., and J. C. Bischof. *Cryobiology* 57:79-83, 2008; Choi, J. H., and J. C. Bischof. *Int. J. Heat Mass Transf* 51:640-649, 2008; and Etheridge et al. *J. Biomech. Eng.* 135:021001: 1-10, 2013.

The enthalpy measured by DSC included some latent heat associated with the glass transition and a small amount of melting (50° C./min is just below the critical warming rate for VS55). The baseline specific heat of VS55 was then extracted based on methods previously described in Choi, J., and J. C. Bischof. *Cryobiology* 60:52-70, 2010; Choi, J. H., and J. C. Bischof. *Cryobiology* 57:79-83, 2008; Choi, J. H., and J. C. Bischof. *Int. J. Heat Mass Transf.* 51:640-649, 2008; and Etheridge et al. *J. Biomech. Eng.* 135:021001: 1-10, 2013. Results are shown in FIG. 15. The density for VS55 included in FIG. 10(*d*) was estimated based on the experimentally determined thermal expansion coefficient for VS55, as a function of temperature, extrapolating from the room temperature density measured at 1069 kg/m³, as described in Jimenez Rios, J. L., and Y. Rabin. *Cryobiology* 52:269-283, 2006.

Cryoprotectant Cooling Protocols

The very high critical cooling rate required to vitrify 6M glycerol (−85° C./min) necessitated direct quenching in liquid nitrogen. While this did provide rapid cooling, the extreme gradients experienced also produced significant cracking in the sample (FIG. 10(*e*)). The lower critical cooling limits for VS55 (−2.5° C./min) allowed for a more nuanced approach.

Figure 11:
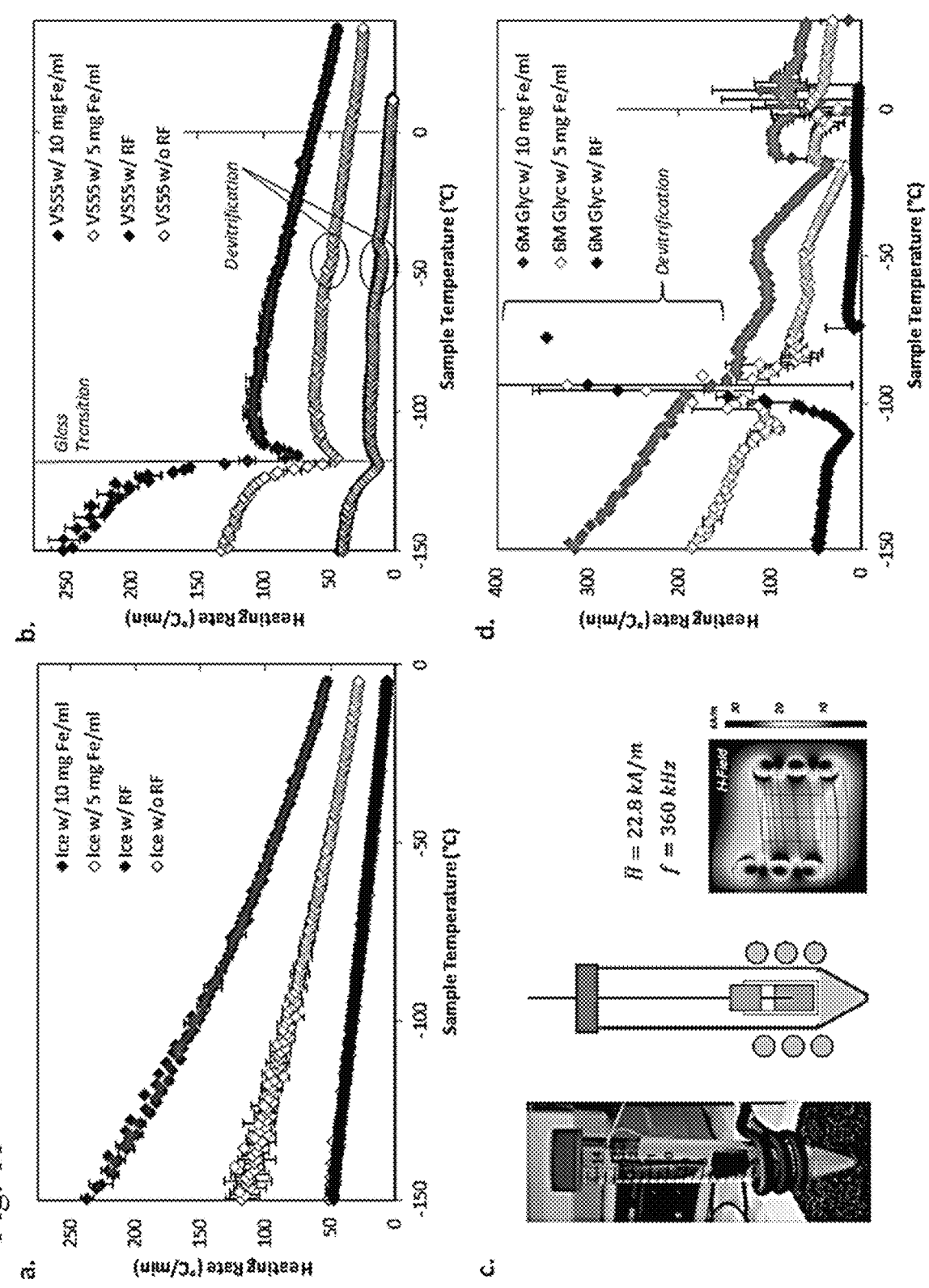
FIG. 11. Radiofrequency heating of mNP-cryoprotectant solutions. The samples were heated from an initial temperature of −192° C. in an inductive coil (c). The cryoprotectant solutions containing mNPs heated at rates up to 300° C./min (a,b,d); these rates were fast enough to reduce devitrification in the 6M glycerol samples (d) and avoid it altogether in the VS55 samples (b).
Figure 16:
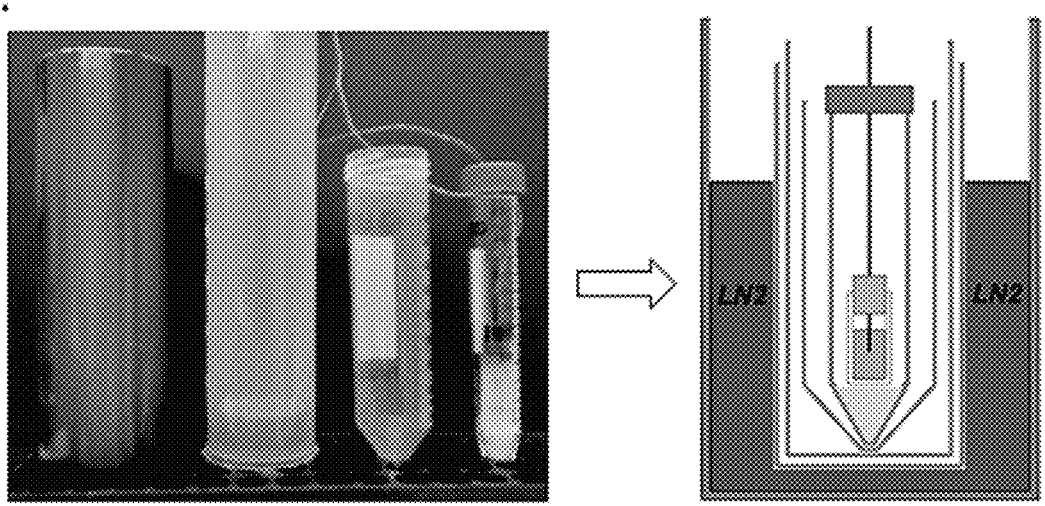
FIG. 16. Cooling protocol for VS55 samples. (a) The VS55 samples were cooled in a liquid nitrogen bath inside a series of containers to provide insulating air gaps and control the cooling rate. (b) An "annealing" step at the glass transition was also included to help relax thermal stresses that might have built up and avoid cracking.
Figure 16:
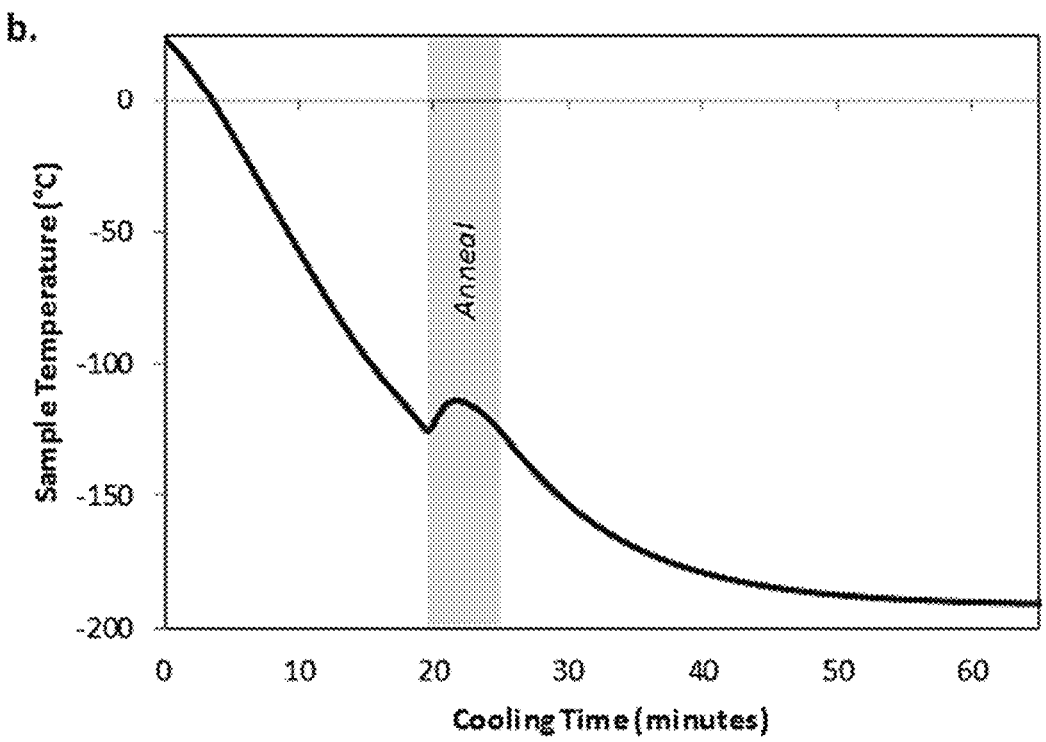

While the samples were still cooled in a liquid nitrogen bath, they were first placed in a series of containers which provided several plastic and air barriers that insulated the cooling rate (FIG. 11(*a*)). In addition, the sample temperature was closely monitored and when it reached the glass transition, the innermost sample container was removed and held out in the room temperature air for 30 seconds, wiped of any frost that had formed (with a gloved hand), and then returned to the cooling container. This process repeatedly produced about a 10° C. increase in the sample temperature before cooling resumed (FIG. 16(*b*)). This should produce an "annealing" effect in the sample, in which some of the thermal stresses induced during cooling are relaxed. Through this process, the VS55 samples were successfully cooled to −192° C. while maintaining an amorphous state without cracking (FIG. 10(*f*)).

Validation of Thermocouple Measurements

Fiber optic thermometry systems are typically used for RF heating measurements, but the plastic probes used with these devices are not rated for use down to cryogenic temperatures. It was therefore necessary to use thermocouples in these studies. However, the strong inductive fields used for heating the mNPs also may produce significant coupling with metals, so we characterized the interference produced in the (type T, copper-constantan) thermocouples. Two investigations demonstrated negligible interference with the ultrafine (40-gauge) thermocouples chosen (OMEGA Engineering, Inc., Stamford, CT). The thermocouples were calibrated at three phase transition temperatures before any measurements were made (liquid nitrogen at −196° C., ice bath at 0° C., and boiling water at 100° C.).

Figure 17:
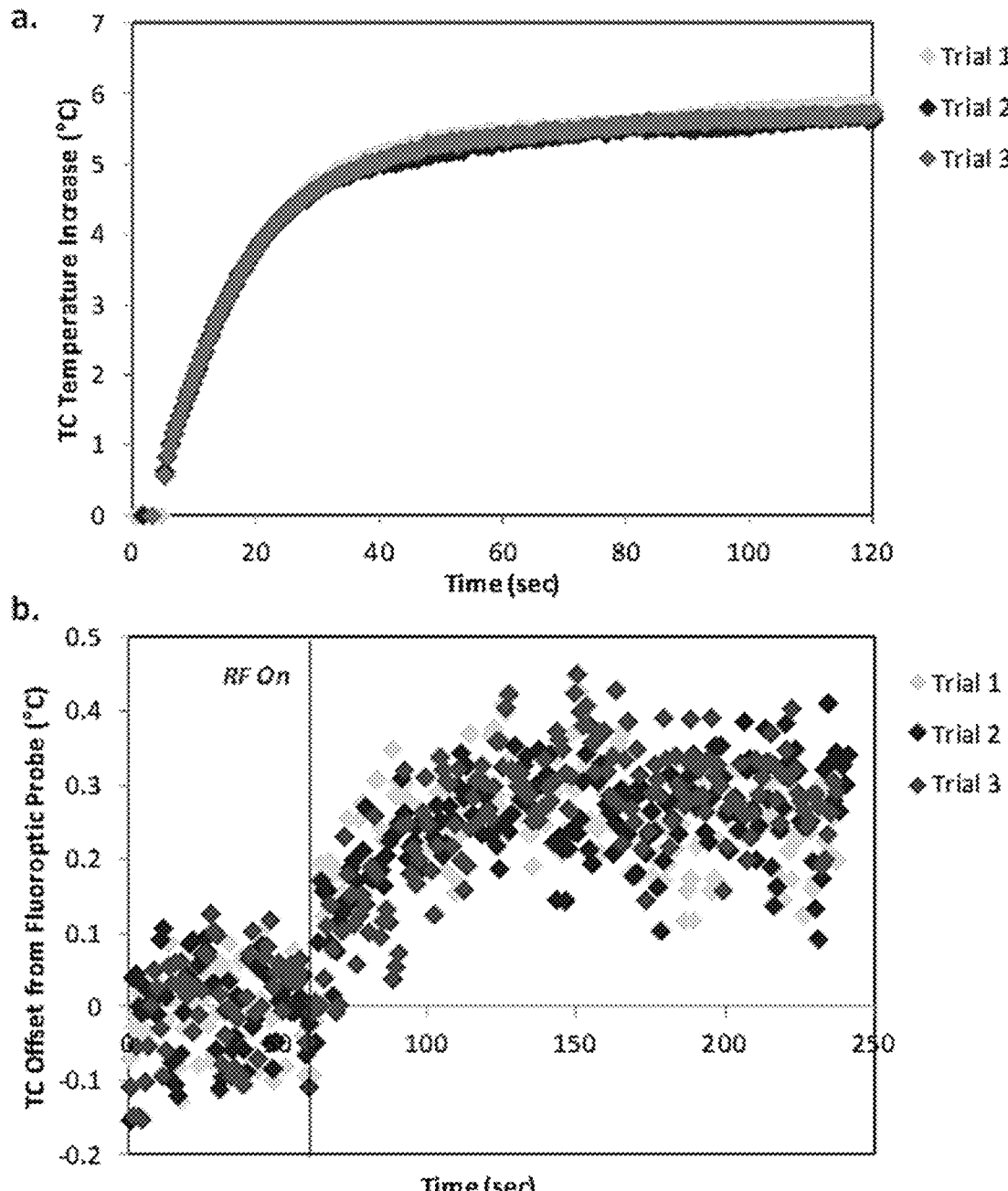
FIG. 17. Measured RF interference in metallic thermocouples. While a measurable temperature rise was observed for insulated thermocouples in the RF field (a), the interference and offset were negligible when compared in aqueous samples (b).

First, metals in an inductive field were subjected to heating. A thermocouple was sandwiched between two pieces of insulation and the tip was centered in the inductive coil. While the thermocouples did experience almost 6° C. of heating under these conditions (FIG. 17(*a*)), the thermal mass of the wires is extremely low and so this equates to an energy of only about 0.5 millijoules. Under the actual experimental conditions, the heat generated in the tip is quickly transferred into the surrounding medium, where this small amount of energy has negligible impact on the measured temperature.

Second, the electrical currents generated in the inductive field also may interfere with the fundamental operation of the thermocouples, which is based on changes in electrical potential. To characterize this, the thermocouples were placed in an uninsulated, 1 ml sample of room temperature water in a cryovial, along with a fluoroptic temperature probe (Luxtron Inc., Santa Clara, CA), and this was placed in the inductive coil. When the field was activated, no noticeable increase in noise was observed (FIG. 17(*b*)). While the fluoroptic probe did not indicate any temperature change, a 0.2-0.3° C. temperature offset was observed for the thermocouples. This may be due, at least in part, to a combination of the thermocouple heating and interference effects. The practical impact, however, is negligible over the large temperature range analyzed in these studies.

One-Dimensional, Non-Uniform Heating Analysis

The following system of partial differential equations was solved numerically in MATHEMATICA (Wolfram Research, Inc., Champagne, IL) utilizing the NDSolve function, based on the problem formulation presented in FIG. 14(*a*).

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of rewarming a cryopreserved biomaterial, the method comprising:
    applying a radiofrequency (RF) field to a cryopreserved composition in a cryopreserved state, the cryopreserved composition comprising a cryopreserved biomaterial and a cryoprotective composition, wherein the cryopreserved biomaterial is suspended in or perfused with the cryoprotective composition, the cryoprotective composition comprising:
    a cryoprotective agent; and
    RF susceptible magnetic nanoparticles comprising iron;
    wherein the magnetic nanoparticles are distributed throughout the cryopreserved composition,
    wherein applying the RF field generates heat at distributed regions throughout the cryopreserved composition by excitation of the distributed magnetic nanoparticles in the RF field, wherein the magnetic nanoparticle distribution is effective for magnetically induced rewarming of the cryopreserved biomaterial that reduces ice crystallization and/or thermal stress throughout the biomaterial during rewarming compared to rewarming by boundary heating or microwave heating,
    wherein the RF field comprises a magnetic field strength of up to about 200 kA/m,
    wherein the concentration of the magnetic nanoparticles in the cryoprotective composition comprises from about 0.01 mg Fe/mL to about 100 mg Fe/mL, and
    wherein the magnetic nanoparticles are superparamagnetic particles having a core diameter of no more than 50 nm and/or ferromagnetic particles having a core diameter of no more than 300 nm.

2. The method of claim 1, wherein the RF field comprises a frequency of up to about 100 MHz.

3. The method of claim 1, wherein the cryopreserved composition has a minimum dimension of at least about 0.1 mm.

4. The method of claim 1, wherein the rewarming by excitation of the distributed magnetic nanoparticles in a RF field is more uniform than by boundary heating or microwave heating.

5. The method of claim 1, wherein the cryopreserved biomaterial is rewarmed at a heating rate of at least about 10° C./minute.

6. The method of claim 1, wherein the cryopreserved biomaterial is perfused with the cryoprotective composition and the concentration of the magnetic nanoparticles in the cryopreserved biomaterial is between about 0.1 mg Fe/mL and about 30 mg Fe/mL.

7. The method of claim 1, wherein the intensity of the RF field during rewarming generates an average thermal gradient of no more than about 1° C./mm within the biomaterial.

8. The method of claim 1, wherein the magnetic nanoparticles are superparamagnetic particles having a core diameter of no more than 20 nm or ferromagnetic particles having a core diameter of no more than 100 nm.

9. The method of claim 1, wherein the magnetic field strength is between about 1 kA/m and about 100 kA/m.

10. The method of claim 1, wherein the cryopreserved composition has a volumetric specific absorption rate (SAR$_v$) of at least 0.1 W/ml.

11. The method of claim 1, wherein the concentration of the magnetic nanoparticles in the cryoprotective composition is from about 0.1 mg Fe/mL to about 100 mg Fe/mL.

12. The method of claim 1, wherein the cryopreserved biomaterial comprises tissue, a whole organ, a cell suspension and/or a cell monolayer.

13. The method of claim 1, further comprising cooling the biomaterial to the cryopreserved state prior to the applying step, wherein the cooling is performed at a rate to promote vitrification and/or minimize cellular and tissue disruption due to ice crystallization within the biomaterial.

14. The method of claim 1, wherein the cryopreserved biomaterial is suspended in the cryoprotective composition and wherein the concentration of the magnetic nanoparticles is between about 1 mg Fe/mL and about 100 mg Fe/mL.

15. The method of claim 1, wherein the magnetic field strength is between about 1 kA/m and about 100 kA/m and wherein the superparamagnetic particles have a core diameter of no more than 20 nm or the ferromagnetic particles have a core diameter of no more than 100 nm.

16. The method of claim 1, wherein the concentration of the magnetic nanoparticles in the cryopreserved composition is between about 0.1 mgFe/mL and about 10 mgFe/mL and the heating rate is at least about 10° C./min.

17. The method of claim 1, wherein the concentration of the magnetic nanoparticles in the cryopreserved composition is between about 1 mgFe/mL and about 50 mgFe/mL and the heating rate is at least about 100° C./min.

18. The method of claim 1, wherein the concentration of the magnetic nanoparticles in the cryopreserved composition is between about 5 mgFe/mL and about 100 mgFe/mL and the heating rate is at least about 1000° C./min.

19. A method of protecting a cryopreserved biomaterial, the method comprising:

applying a RF field to a cryopreserved composition comprising a cryoprotective composition and a cryopreserved biomaterial, wherein the cryoprotective composition comprises:

a cryoprotective agent; and

RF susceptible magnetic nanoparticles comprising iron;

wherein the magnetic nanoparticles are distributed throughout the cryopreserved composition, wherein applying the RF field generates heat at distributed regions throughout the cryopreserved composition by excitation of the distributed magnetic nanoparticles, wherein the magnetic nanoparticle distribution is effective for magnetically induced rewarming of the cryopreserved biomaterial that reduces ice crystallization and/or thermal stress throughout the biomaterial during rewarming compared to boundary heating or microwave heating when excited with a magnetic field strength of up to about 100 kA/m, wherein the magnetic nanoparticles are superparamagnetic particles having a core diameter of no more than 20 nm and/or ferromagnetic particles having a core diameter of no more than 100 nm, wherein the concentration of the magnetic nanoparticles in the cryoprotective composition is between about 0.1 mg Fe/mL to about 100 mg Fe/mL, wherein the cryopreserved composition has a volumetric specific absorption rate (SAR$_v$) of at least 0.1 W/ml.

20. The method of claim 19, wherein the method further comprises suspending the biomaterial in the cryoprotective composition; and cooling the biomaterial to a cryopreserved state to form the cryopreserved composition prior to the applying step.

21. The method of claim 19, wherein the method further comprises perfusing the biomaterial with the cryoprotective composition;

suspending the perfused biomaterial; and cooling the biomaterial to a cryopreserved state to form the cryopreserved composition prior to the applying step.

22. The method of claim 1, wherein the biomaterial is perfused with the cryoprotective composition and wherein the perfused biomaterial is suspended in the cryoprotective composition.

* * * * *